US011181318B2

(12) United States Patent
Heffernan et al.

(10) Patent No.: US 11,181,318 B2
(45) Date of Patent: Nov. 23, 2021

(54) WOOD HEATING SYSTEM AND METHOD

(71) Applicants: William John Baxter Heffernan, Christchurch (NZ); Nurzhan Nursultanov, Christchurch (NZ); Marinus Johannes Wilhelmus Maria Ryan Van Herel, Christchurch (NZ)

(72) Inventors: William John Baxter Heffernan, Christchurch (NZ); Nurzhan Nursultanov, Christchurch (NZ); Marinus Johannes Wilhelmus Maria Ryan Van Herel, Christchurch (NZ)

(73) Assignee: The University of Canterbury of Ilam Road, Christchurch (NZ)

( * ) Notice: Subject to any disclaimer, the term of this patent is extended or adjusted under 35 U.S.C. 154(b) by 0 days.

(21) Appl. No.: 16/494,717

(22) PCT Filed: Mar. 14, 2018

(86) PCT No.: PCT/NZ2018/050029
§ 371 (c)(1),
(2) Date: Sep. 16, 2019

(87) PCT Pub. No.: WO2018/169415
PCT Pub. Date: Sep. 20, 2018

(65) Prior Publication Data
US 2020/0103168 A1 Apr. 2, 2020

(30) Foreign Application Priority Data
Mar. 14, 2017 (NZ) .......................... 730025

(51) Int. Cl.
*F26B 3/353* (2006.01)
*B27K 5/00* (2006.01)
(Continued)

(52) U.S. Cl.
CPC .............. *F26B 3/353* (2013.01); *B27K 5/001* (2013.01); *B27K 5/0015* (2013.01); *F26B 23/06* (2013.01);
(Continued)

(58) Field of Classification Search
CPC ........ F26B 3/353; F26B 23/06; F26B 25/225; F26B 2210/16; B27K 5/001; B27K 5/0015; G01N 33/46
(Continued)

(56) References Cited

U.S. PATENT DOCUMENTS 1,899,233 A 2/1933 Reilly
2,567,983 A 9/1951 Wood
(Continued)

FOREIGN PATENT DOCUMENTS

CA 2238353 11/1999
CA 2683167 4/2010
(Continued)

OTHER PUBLICATIONS

Fleischer et al., "Heating Veneer Logs Electrically," United States Department of Agriculture, Forest Service, Forest Products Laboratory, Madison, 1953, pp. 1-13.
(Continued)

*Primary Examiner* — Stephen M Gravini
(74) *Attorney, Agent, or Firm* — Barnes & Thornburg LLP

(57) ABSTRACT

A wood heating system comprises an electric power source, a first electrode assembly, a second electrode assembly, and a control system. The first electrode assembly is connected to the electric power source and is adapted to make electrical contact with a first end of a wood length to apply electric power to the wood length. The first electrode assembly comprises at least two electrode segments. The second
(Continued)

electrode assembly is adapted to make electrical contact with a second end of the wood length. The control system is adapted to selectively connect/disconnect electric power flow between the electric power source and at least one electrode segment of the first electrode assembly.

28 Claims, 14 Drawing Sheets

(51) Int. Cl.
*F26B 23/06* (2006.01)
*F26B 25/22* (2006.01)
*G01N 33/46* (2006.01)

(52) U.S. Cl.
CPC ........... *F26B 25/225* (2013.01); *G01N 33/46* (2013.01); *F26B 2210/16* (2013.01)

(58) Field of Classification Search
USPC .......................................................... 34/282
See application file for complete search history.

(56) References Cited

U.S. PATENT DOCUMENTS

| | | | | |
|---|---|---|---|---|
| 3,807,055 | A * | 4/1974 | Kraxberger | F26B 25/22 34/402 |
| 4,580,233 | A * | 4/1986 | Parker | G01N 33/46 324/666 |
| 6,577,143 | B2 * | 6/2003 | Arsenault | G01N 27/048 324/689 |
| 6,703,847 | B2 * | 3/2004 | Venter | G01N 27/223 324/521 |
| 6,784,672 | B2 * | 8/2004 | Steele | G01N 27/02 324/663 |
| 6,989,678 | B2 * | 1/2006 | Venter | G01N 27/223 324/521 |
| 7,814,799 | B2 | 10/2010 | Tiitta et al. | |
| 10,757,960 | B2 * | 9/2020 | Tanaka | A47J 37/1266 |
| 2003/0001595 | A1 | 1/2003 | Steele et al. | |
| 2014/0009174 | A1 | 1/2014 | Youssi et al. | |
| 2020/0103168 | A1 * | 4/2020 | Heffernan | B27K 1/00 |

FOREIGN PATENT DOCUMENTS

| | | | |
|---|---|---|---|
| CN | 2792737 | 7/2006 | |
| CN | 101655394 | 2/2010 | |
| CN | 201749100 U | 2/2011 | |
| CN | 203586881 U | 5/2014 | |
| GB | 2159613 | 12/1985 | |
| JP | H11-14251 | 1/1999 | |
| KR | 100813673 | 3/2008 | |
| WO | 2003/037107 | 5/2003 | |
| WO | WO 2007/028856 | 3/2007 | |
| WO | 2008/028992 | 3/2008 | |
| WO | WO 2009/125058 | 10/2009 | |
| WO | WO-2018169415 A1 * | 9/2018 | .............. F26B 3/353 |

OTHER PUBLICATIONS

Heffernan, "Practical Application of Joule Heating to the Sterilization of Plantation Grown *Pinus radiata* Logs," Electric Power Engineering Centre, (EPECentre), EEA Conference & Exhibition, University of Canterbury, 2013, pages i-ii and 1-10 (2013).
Search Report & Written Opinion issued in Int'l Appl. No. PCT/NZ2018/050029 (2018).
Extended European Search Report and Opinion issued in Appl. No. EP18766660 (dated Nov. 20, 2020).
Heffernan et al., "Joule Heating of logs for phytosanitary purposes and timber processing pre-treatment," Advanced Materials Letters, 9(11), 767-775 (2018).
Office Action issued in Appl. CN201880023122 (2020).
Perré, "Electrical heating of green logs using Joule's effect: a comprehensive computational model used to find a suitable electrode design," Wood Sci. Technol. 38: 429-449 (2004).

* cited by examiner

WOOD HEATING SYSTEM AND METHOD

CROSS REFERENCE TO RELATED APPLICATIONS

This application is a U.S. nationalization under 35 U.S.C. § 371 of International Application No. PCT/NZ2018/050029, filed 14 Mar. 2018, which claims priority to New Zealand Patent Application No. 730025, filed 14 Mar. 2017. The disclosures set forth in the referenced applications are incorporated herein by reference in their entireties.

FIELD OF THE INVENTION

The invention relates to a wood heating system, a method of determining energy to be applied to a wood length, and a control system adapted to determine energy applied to a wood length. The invention is particularly suited to heating unseasoned timber logs for phytosanitary treatment and/or timber veneer peeling.

BACKGROUND OF THE INVENTION

It is known to heat unseasoned timber logs for various applications such as wood sterilisation, colouration, debarking, or drying.

PCT patent application publication WO 03/037107, for example, discloses a method of electrically heating a log for the purposes of wood sterilisation, colouration, and debarking.

First and second electrodes are arranged in electrical contact with wood to be treated via an electrically conductive material such as steel wool. A voltage is applied across the electrodes. The wood is typically heated up to temperatures as high as 200° C.

A 3% KCl conductive gel is applied to the electrodes. Water is pumped over the ends of the log to provide electrical conductivity.

PCT patent application publication WO 2008/028992 and WO 2009/125058, for example, disclose apparatus for drying wood by conducting electric energy by means of electrodes directly to the log to be dried. The vapour generated in a centre of the log pushes out liquids in the log via capillaries within the wood.

The electrodes are arranged to contact the sides of the log rather than the ends. A gel-type material may be used for conducting electricity.

Logs tend to include non-uniformities such as knots and resin pockets. Application of known electric wood heating techniques to such logs has the potential to cause formation of hot and cold regions inside the log. Furthermore, known electric wood heating techniques have the potential to achieve sub-optimal electrical contact between the electrodes and the surface of the log.

It is an object of at least preferred embodiments of the present invention to address some of the aforementioned disadvantages. An additional or alternative object is to at least provide the public with a useful choice.

SUMMARY OF THE INVENTION

In accordance with an aspect of the invention, a wood heating system comprises an electric power source; a first electrode assembly connected to the electric power source and adapted to make electrical contact with a first end of a wood length to apply electric power to the wood length, the first electrode assembly comprising at least two electrode segments; a second electrode assembly adapted to make electrical contact with a second end of the wood length; and a control system adapted to selectively connect/disconnect electric power flow between the electric power source and at least one electrode segment of the first electrode assembly.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

In an embodiment, the at least two electrode segments of the first electrode assembly comprise respective generally arcuate segments extending at least part of the way around a substantially flat face, the flat face adapted to contact the first end of the wood length.

In an embodiment the arcuate segments are positioned between respective pairs of concentric rings extending at least part of the way around the substantially flat face.

In an embodiment, the at least two electrode segments of the first electrode assembly comprise respective generally concentric ring-shaped segments extending around a substantially flat face, the flat face adapted to contact the first end of the wood length.

In an embodiment, the at least two electrode segments of the first electrode assembly comprise respective generally hexagonal shaped segments forming a substantially flat face, the flat face adapted to contact the first end of the wood length.

In an embodiment, the at least two electrode segments of the first electrode assembly comprise respective generally square shaped segments forming a substantially flat face, the flat face adapted to contact the first end of the wood length.

In an embodiment, at least two of the at least two electrode segments of the first electrode assembly have substantially equal surface areas within the flat face.

In an embodiment, at least two of the at least two electrode segments have different surface areas within the flat face.

In an embodiment, at least two of the at least two electrode segments of the first electrode assembly are electrically insulated from each other.

In an embodiment, a surface area of the face adapted to contact the first end of the wood length is larger than a surface area of the first end of the wood length.

In an embodiment, the first electrode assembly is provided with a compressible medium interposable between the flat face of the first electrode assembly and the first end of the wood length. In an embodiment the compressible medium comprises a porous structural pad. In an embodiment the porous pad comprises an open-cell foam pad.

In an embodiment, the compressible medium is electrically conductive.

In an embodiment, the wood heating system further comprises a wetting system adapted to apply an electrically conductive fluid to the compressible medium. In an embodiment the wetting system is adapted to wet the compressible medium with the electrically conductive fluid. In an embodiment the wetting system is adapted to saturate the compressible medium with the electrically conductive fluid. In an embodiment the electrically conductive fluid comprises an electrically conductive gel. In an embodiment the electrically conductive gel comprises an aqueous sodium chloride solution and *psyllium* husk. In an embodiment the electrically conductive gel comprises an aqueous sodium chloride solution and carboxymethyl cellulose. In an embodiment the electrically conductive gel comprises another chemical salt solution and *psyllium* husk. In an embodiment the electrically conductive gel comprises only water and *psyllium* husk. In an embodiment the electrical conductivity of the electrically conductive gel is approximately matched to the electrical conductivity, in the axial direction, of the most conductive region of the wood length to be heated. In an embodiment the electrically conductive gel is pre-heated.

In an embodiment, the wetting system comprises a pump adapted to apply the electrically conductive fluid to the compressible medium; a collector adapted to collect and store excess electrically conductive fluid applied to the compressible medium; and a filtration unit adapted to filter the electrically conductive fluid for the pump to apply the filtered electrically conductive fluid to the compressible medium.

In an embodiment, the wetting system comprises an electrically conductive fluid-filled tank into which the compressible medium, detached from the electrode assembly and held in a suitable frame, is immersed, using a suitable actuator. The compressible medium is compressed (e.g. by a pneumatic actuator), expelling any air, and then released, taking up a full load of fluid. The framed compressible medium is then lifted from the tank, by the actuator, into position between electrode assembly and the log end.

In an embodiment, at least two of the at least two electrode segments of the first electrode assembly are connected to the electric power source.

In an embodiment, the wood heating system further comprises a chamber adapted to receive the wood length. In an embodiment the chamber is thermally insulated. In an embodiment the temperature within the chamber is actively controlled. In an embodiment the humidity within the chamber is actively controlled. In an embodiment the chamber includes a forced air circulation system. In an embodiment the chamber includes jets adapted to apply a fluid to the surface of the wood length. In an embodiment the jets are adapted to apply a fine mist of water to the surface of the wood length.

In an embodiment, the control system is adapted to monitor the electric power being introduced to the wood length by the first electrode assembly and the second electrode assembly.

In an embodiment, the wood heating system further comprises at least one actuator adapted to apply the first electrode assembly to the first end of the wood length. In an embodiment the at least one actuator comprises one of a pneumatic ram, a hydraulic ram, a compression spring.

In an embodiment, the second electrode assembly comprises at least two electrode segments. In an embodiment the second electrode assembly comprises the same number of electrode segments as the first electrode assembly. In an embodiment the second electrode assembly comprises electrode segments of generally the same shape as the electrode segments of the first electrode assembly. In an embodiment the second electrode assembly comprises electrode segments of generally the same size as the electrode segments of the first electrode assembly.

In an embodiment, the second electrode assembly comprises a plurality of electrode segments forming a substantially flat face, the flat face adapted to contact the second end of the wood length.

In an embodiment the flat face of the first electrode assembly and the flat face of the second electrode assembly generally face each other when the first electrode assembly makes contact with the first end of the log and the second electrode assembly makes contact with the second end of the log.

In an embodiment, the electric power source comprises one of an AC voltage source, a DC voltage source, an AC/DC voltage source, an AC current source, a DC current source, an AC/DC current source, an AC Z-source, a DC Z-source, an AC/DC Z-source.

In an embodiment the electric power source is configured to supply constant power to the wood length, despite the resistance of the wood length changing with temperature.

In an embodiment the resistance of the wood length is in the range 100Ω to 10 kΩ over the temperature range experienced.

In an embodiment the electric power source is configured to provide electric field strengths in the range of 0.5 to 20 kVm$^{-1}$ across the wood length.

In an embodiment, the electric power source is configured to provide an average current density in the range of 50 to 500 Am$^{-2}$ to conductive regions of the wood length, for instance sapwood.

In an embodiment the electric power source supplies a power density in the range of 100 to 2000 kWm$^{-3}$ to the wood length.

In an embodiment, the wood length comprises one of a length of sawn timber, a timber log (unseasoned, seasoned, or partially seasoned), a length of roundwood (for example a fence-post or power-pole).

In accordance with a further aspect of the invention, a method of determining energy to be applied to a wood length comprises receiving at least one wood length parameter; receiving a plurality of process parameters, the process parameters including at least one control volume associated to the wood length and at least one termination condition; receiving at least one temperature parameter, the at least one temperature parameter including a temperature of at least one of the at least one control volumes; and, until satisfaction of the at least one termination condition, calculating an electrical conductivity of at least one of the at least one control volumes, calculating at least one power parameter, and determining a temperature change in at least one of the at least one control volumes. The term 'control volume' as used in this description and claims refers to any element used in any discretized computational method.

In an embodiment, the at least one wood length parameter comprise(s) one or more of large end diameter (LED), small end diameter (SED), heartwood diameter at a large end (LED_HW), heartwood diameter at a small end (SED_HW), sapwood moisture content (SMC), heartwood moisture content (HMC), basic densities (BD), log mass, volume (V), equation(s) defining axial electrical conductivity of timber (σ) as a function of temperature In an embodiment, the process parameters comprise one or more of electrical power (P), total energy ($Q_T$), energy of an excitation period (Q), number of excitation periods ($N_{exc}$), relaxation interval, number of control volumes in a heartwood region of the wood length, number of control volumes in a sapwood region of the wood length, multiplication coefficient for electrical conductivity (α).

In an embodiment, the at least one temperature parameter comprise(s) one or more of chamber temperature, temperature of at least one control volume in the heartwood region of the wood length, temperature of at least one control volume in the sapwood region of the wood length.

In an embodiment, the at least one power parameter comprise(s) one or more of a resistance of at least one control volume, a voltage across at least one control volume, a current through at least one control volume, a power dissipation density (S) in at least one control volume.

In accordance with a further aspect of the invention, a control system adapted to determine energy applied to a wood length comprises a processor configured to receive at least one wood length parameter; receive a plurality of process parameters, the at least one process parameter including at least one control volume associated to the wood length and at least one termination condition; receive at least one temperature parameter, the at least one temperature parameter including a temperature of at least one of the at least one control volumes; and, until satisfaction of the at least one termination condition, calculate an electrical conductivity of at least one of the at least one control volume, calculate at least one power parameter, and determine a temperature change in at least one of the at least one control volume.

In an embodiment the control system applies the energy excitation periods and relaxation intervals determined by the method. In an embodiment the control system measures the total resistance of the wood length in real-time during the excitation periods. In an embodiment the control system verifies that the total resistance versus time varies according to the results of the method within a predefined tolerance. A suitable predefined tolerance may be 10% of absolute value.

In an embodiment the processor is further configured to measure the current density in, and/or resistance of, at least one control volume, or set of control volumes, during the excitation periods. In an embodiment the processor is further configured to verify that the current density and/or resistance of at least one control volume, or set of control volumes, varies according to the results of the method within a predefined tolerance. A suitable predefined tolerance may be 10% of absolute value.

In accordance with a further aspect of the invention, an electromagnetic shielding system comprises an electric power source; a first electrode assembly connected to the electric power source and adapted to make electrical contact with a first end of a wood length to apply electric power to the wood length; and an electromagnetic (EM) screen that surrounds a wood length, the electromagnetic screen adapted to receive electric current passing in a first direction through the wood length, and transmit electric current in a second direction through the electromagnetic screen, the first direction opposite to the second direction.

In an embodiment, the electromagnetic shielding system further comprises a high voltage (HV) winding adapted to supply electric power to the first electrode assembly.

In an embodiment, the HV winding is adapted to make electrical contact with the first electrode assembly via the centre conductor of a coaxial or triaxial cable. In an embodiment, the EM screen is adapted to make electrical contact with the second electrode assembly and an earthed end of the HV winding.

In an embodiment, the EM screen around the log is a conducting cylinder at approximately ground potential.

In an embodiment, the cylinder is made up from a plurality of individual conductors with small series balancing impedances to balance the current in each conductor.

In an embodiment, the electromagnetic shielding system further comprises an electrostatic (ES) screen.

In an embodiment, the ES screen returns displacement currents, caused by alternating voltage on the log surface, directly to supply ground rather than allowing them to flow through the EM screen.

In an embodiment, a primary winding of a current transformer (CT), with unity turns ratio, is placed in series with an earth end of the HV winding.

In an embodiment, a secondary winding of the current transformer, which may be earthed, drives an exact replica of the log current around the EM screen to oppose the log current and cancel the external magnetic field.

In an embodiment, the current transformer is adapted to drive the burden impedance of the EM screen, including any balancing impedances.

In an embodiment, an ES screen is employed to permit the EM screen to float or be connected to any convenient potential, rather than being grounded.

In an embodiment a centre-ground bipolar HV supply is connected to the log.

In an embodiment, the current transformer (CT) supplies an exact replica of the log current, to cancel the external magnetic field, and allows the EM screen to be at any desired potential, including ground, while the ES screen prevents any displacement currents flowing through the CT windings.

In an embodiment, the CT supplies an approximate replica of the log current, to partially cancel the external magnetic field. The error difference between the log current and the partial cancellation current is measured, for example by a further CT, and is input to a servo amplifier which drives an additional appropriate nulling current around the EM screen to fully cancel the external magnetic field.

In an embodiment, a current transformer implements an active system rather than a passive system by providing a signal corresponding to the log current to a current amplifier.

In an embodiment, the amplifier drives a compensating current through the EM screen to eliminate external magnetic field. The electromagnetic screen may be grounded, or held at any other desired potential.

In an embodiment, the EM and ES screens are combined and incorporated in the form of two half-pipes. Each half-pipe includes an inner insulating layer followed by a conductive ES screen.

In an embodiment, the ES screen is formed from a thin sheet or foil of copper, aluminium, or other electrically conductive material.

In an embodiment, a second insulating layer isolates the ES screen from the outer EM screen.

In an embodiment, when joined, the two half-pipes form an electromagnetic chamber.

In accordance with a further aspect of the invention, a wood heating process comprises a wood heating system, a control system and a screening system having a top half-pipe and a bottom half-pipe. With the top half-pipe lifted out of the way, a log enters the system from a conveyor before the top half-pipe is again lowered into place. A first electrode assembly and a second electrode assembly slide within a tube formed from the two half-pipes.

In accordance with a further aspect of the invention, a wood heating process comprises a wood heating system, a control system and a screening system having a top half-pipe and a bottom half-pipe. The top half-pipe is fixed in place above a conveyor and the log is raised into a centred position on insulating supports driven by pneumatic or hydraulic rams. The bottom half-pipe is then raised into place before electrical excitation is applied.

In an embodiment, the pneumatic or hydraulic rams are fitted with load cells, such that the mass of the log is measured at the start and/or at the end of an excitation.

In an embodiment spacing between the electrode assemblies is adjusted by a pair of pneumatic or hydraulic rams.

The invention in one aspect comprises several steps. The relation of one or more of such steps with respect to each of the others, the apparatus embodying features of construction, and combinations of elements and arrangement of parts that are adapted to affect such steps, are all exemplified in the following detailed disclosure.

The terms 'component', 'module', 'system', 'interface', and/or the like as used in this specification in relation to a processor are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The term 'connected to' as used in this specification in relation to data or signal transfer includes all direct or indirect types of communication, including wired and wireless, via a cellular network, via a data bus, or any other computer structure. It is envisaged that there may be intervening elements between the connected integers. Variants such as 'in communication with', 'joined to', and 'attached to' are to be interpreted in a similar manner. Related terms such as 'connecting' and 'in connection with' are to be interpreted in the same manner.

The term 'connected to' as used in this specification in relation to electric power envisages that there may be intervening elements between the connected integers. Variants such as 'in communication with', 'joined to', and 'attached to' are to be interpreted in a similar manner. Related terms such as 'connecting' and 'in connection with' are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

In addition, where features or aspects of the invention are described in terms of Markush groups, those persons skilled in the art will appreciate that the invention is also thereby described in terms of any individual member or subgroup of members of the Markush group.

As used herein, '(s)' following a noun means the plural and/or singular forms of the noun.

As used herein, the term 'and/or' means 'and' or 'or' or both.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents or such sources of information is not to be construed as an admission that such documents or such sources of information, in any jurisdiction, are prior art or form part of the common general knowledge in the art.

In the description in this specification reference may be made to subject matter which is not within the scope of the appended claims. That subject matter should be readily identifiable by a person skilled in the art and may assist in putting into practice the invention as defined in the presently appended claims.

Although the present invention is broadly as defined above, those persons skilled in the art will appreciate that the invention is not limited thereto and that the invention also includes embodiments of which the following description gives examples.

BRIEF DESCRIPTION OF THE DRAWINGS

Preferred forms of the wood heating system, method of determining energy to be applied to a wood length, and control system adapted to determine energy applied to a wood length will now be described by way of example only with reference to the accompanying figures in which.

DETAILED DESCRIPTION

Figure 1:
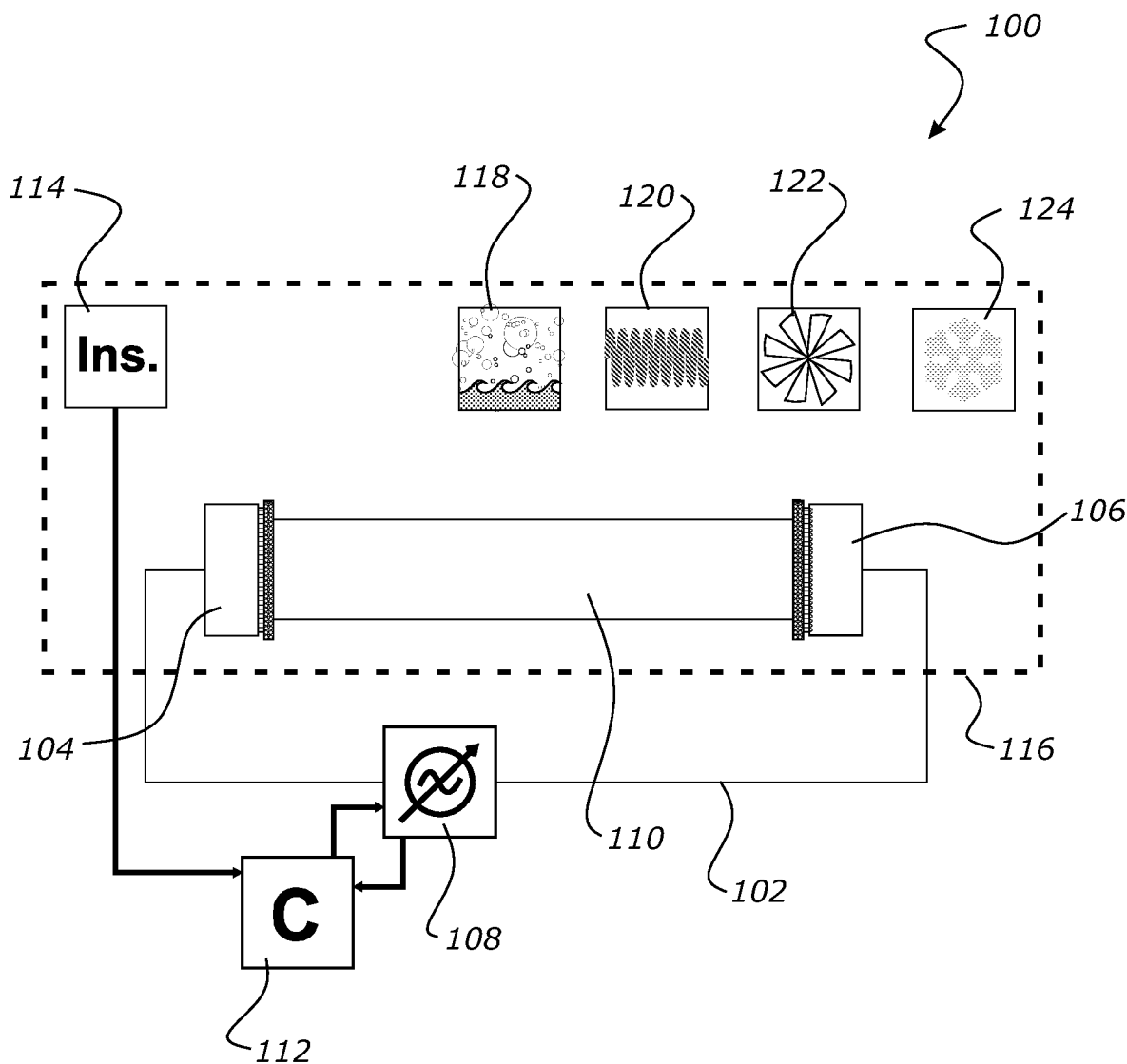
FIG. 1 shows an example of a wood heating system.

FIG. 1 shows an example of a wood heating system 100. The system 100 includes an electric circuit 102. The circuit 102 includes a first electrode assembly 104 and a second electrode assembly 106.

The circuit further includes an electric power source 108. In an embodiment the power source 108 comprises an AC voltage source, a DC voltage source, or an AC/DC voltage source. In an embodiment the power source 108 comprises an AC current source, a DC current source, or an AC/DC current source. In an embodiment the power source 108 comprises an AC Z-source, a DC Z-source, or an AC/DC Z-source.

In an embodiment, where the electric power source 108 provides AC electric power, the frequency matches a locally available mains supply. In an embodiment the frequency is not harmonically related to the mains supply. In an embodiment the frequency is in the approximate range of 50-75 Hz. In an embodiment the frequency is in the approximate range of 375 Hz to 425 Hz. In an embodiment the frequency is approximately 405 Hz.

In an embodiment the first electrode assembly 104 is adapted to apply electric power from the power source 108 to a first end of a wood length or log 110. In an embodiment, the wood length 110 comprises one of a length of sawn timber, a timber log (unseasoned, seasoned, or partially seasoned), a length of roundwood (for example a fence-post or power-pole).

In an embodiment the electric power source 108 is configured to supply constant power to the wood length 110, despite the resistance of the wood length changing with temperature.

In an embodiment the resistance of the wood length 110 is in the range 100Ω to 10 kΩ over the temperature range experienced.

In an embodiment the electric power source 108 is configured to provide electric field strengths in the range of 0.5 to 20 $kVm^{-1}$ across the wood length 110.

In an embodiment, the electric power source is configured to provide an average current density in the range of 50 to 500 $Am^{-2}$ to conductive regions of the wood length 110, for example sapwood.

In an embodiment the electric power source supplies a power density in the range of 100 to 2000 $kWm^{-3}$ to the wood length 110.

The first electrode assembly 104 is shown in contact with a first end of the wood length 110 and the second electrode assembly 106 is shown in contact with a second end of the wood length 110. As will be described below, a compressible medium is optionally interposed between first electrode assembly 104 and the first end of the wood length 110, and between second electrode assembly 106 and the second end of the wood length 110.

First electrode assembly 104 has a substantially flat face that generally faces a substantially flat face of the second electrode assembly when the first electrode assembly 104 is in electrical contact with the first end of the wood length 110 and when the second electrode assembly 106 is in electrical contact with the second end of the wood length 110.

In an embodiment the second electrode assembly 106 is adapted to make electrical contact with a second end of the log 110. In an embodiment the log 110 conveys electric power from the first electrode assembly 104 to the second electrode assembly 106. In an embodiment the first electrode assembly 104 is adapted to receive electric power conveyed through the log 110 from the second electrode assembly 106.

In an embodiment one or both of the first electrode assembly 104 and the second electrode assembly 106 in turn comprise at least two electrode segments. Examples of constructions of the first electrode assembly 104 and the second electrode assembly 106 are further described below.

In an embodiment a control system or controller 112 is adapted to selectively connect and/or disconnect current flow between the power source 108 and at least one electrode segment of the first electrode assembly 104. In an embodiment the controller 112 is adapted to selectively connect and/or disconnect current flow between the power source 108 and at least one electrode segment of the second electrode assembly 106.

The controller 112 operates to change the voltage applied to the log 110 to allow a current to flow at an appropriate or desired power level. As will be described below, the resistance of the log 110 changes with respect to temperature of the material forming the log 110.

In an embodiment the controller 112 includes computer executable instructions or software to calculate the energy to be applied to the log 110. In an embodiment the amount of energy to be applied to the log 110 is at least partly determined from a set of measurements made on the log 110 prior to the application of electric power.

In an embodiment a measurement system 114 is connected to the controller 112. The measurement system 114 is adapted to obtain one or more measurements of the log 110. These measurements include, but are not limited to, one or more of total mass, heartwood diameter, total diameter, initial temperature of the log 110.

In an embodiment the wood heating system 100 includes a chamber 116 adapted to receive the log 110. In an embodiment the chamber 116 is thermally insulated.

In an embodiment the measurement system 114 is adapted to measure one or more environmental conditions within the chamber 116. Examples of environmental conditions include temperature and humidity. In an embodiment the ambient temperature within the chamber 116 is able to be elevated. In an embodiment the ambient temperature is elevated in order to destroy insects and other parasites located on an outside surface of the log 110. In an embodiment the ambient temperature is elevated to preferentially increase the electrical conductivity of the outer part of the log 110.

In an embodiment the wood heating system 100 includes steam jets 118 adapted to actively introduce steam into the chamber 116. It is desirable to introduce steam into the chamber 116 for some applications in order to maintain a high ambient humidity within the chamber 116. A high ambient humidity has the potential to minimise the loss of moisture from the log 110 during log heating.

In an embodiment the wood heating system 100 includes a heating element 120. In an embodiment temperature elevation occurs within the chamber 116 due to the process of applying current to the log 110. In an embodiment the heating element 120 assists with temperature elevation.

In an embodiment the wood heating system 100 includes a fan or equivalent forced air circulation system 122 adapted to force circulation of air within the chamber 116. The circulation of air within the chamber 116 has the potential to ensure all parts of the chamber 116 reach uniformly a required temperature and/or humidity.

In an embodiment the wood heating system 100 includes a cooling element 124. The cooling element 124 in an embodiment comprises a plurality of jets adapted to apply a fine mist of water to a surface of the log 110. Evaporation of the water from the surface of the log 110 has the potential to lower the temperature of the log 110. In an embodiment the temperature is lowered to preferentially reduce the electrical conductivity of the outer part of the log 110.

As described above, electric power is applied via first electrode assembly 104 and/or second electrode assembly 106 to the log 110.

In an embodiment the system 100 is adapted to individually monitor the power flowing through at least some of the electrode segments of electrode assembly 104 and/or 106. In an embodiment the controller 112 is adapted to individually monitor the power flowing through each of the electrode segments of electrode assembly 104 and/or 106.

In an embodiment the controller 112 is adapted to selectively disconnect or connect the electric power flow from or to one or more of the electrode segments of electrode assembly 104 and/or 106.

In an embodiment the system 100 includes at least one actuator (not shown) adapted to apply the first electrode assembly 104 and/or the second electrode assembly 106 to an end of the log 110. In an embodiment the actuator comprises one of a pneumatic ram, a hydraulic ram, and a compression spring.

In an embodiment the controller 112 determines whether proper contact has been made between electrode assembly 104 and/or 106 and the log 110. Monitoring the distribution of the current has the potential to be able to determine in which region of the log 110 the current is entering or exiting. This in turn gives a picture of the current and therefore power distribution inside the log 110.

Figure 2:
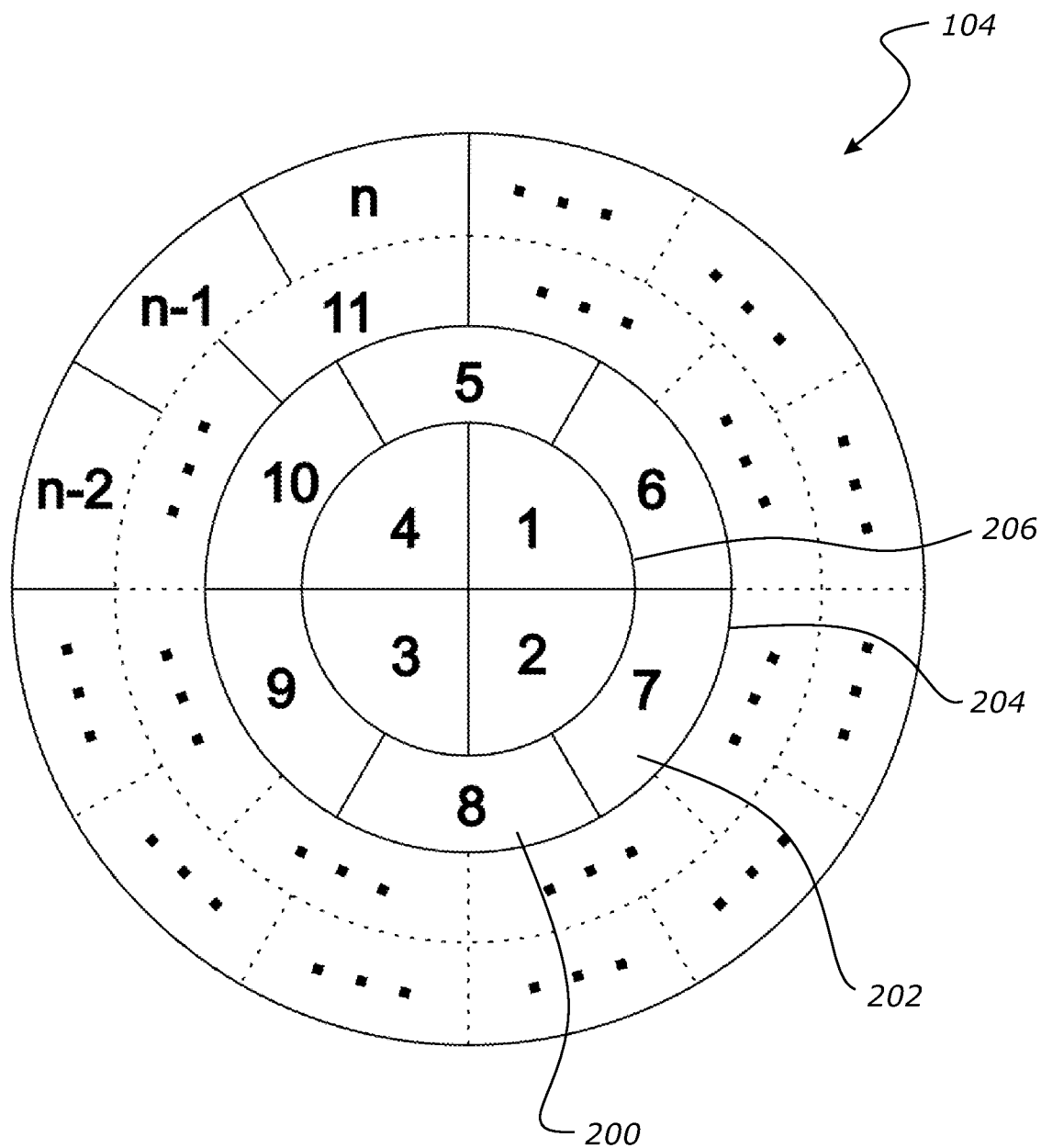
FIG. 2 shows an example of the face of a segmented electrode assembly.

FIG. 2 shows an example of a face of a first segmented electrode assembly 104. In an embodiment second electrode assembly 106 has the same configuration as first electrode assembly 104. In an embodiment the second electrode assembly 106 has a configuration that differs from that of the first electrode assembly 104.

As shown in FIG. 2, in an embodiment the first electrode assembly 104 comprises respective generally arcuate segments. Electrode segments 200 and 202 for example extend at least part of the way around a substantially circular flat face of the first electrode assembly 104. Electrode segments 200 and 202 are shown positioned between a pair of concentric rings extending around the flat face.

In the embodiment shown in FIG. 2, electrode segments 200 and 202 have substantially the same surface area. In an embodiment the electrode segments 200 and 202 have substantially the same surface area as the other electrode segments positioned between concentric rings 204 and 206. In an embodiment the electrode segments positioned between any pair of concentric rings have substantially the same surface area. In an embodiment the electrode segments positioned between a pair of concentric rings do not have substantially the same surface area.

Although the electrode segments are shown as arcuate, it will be appreciated that the electrode segments are not required to be arcuate. In an embodiment the electrode segments comprise respective generally concentric ring-shaped segments extending around the flat face. In an embodiment the electrode segments comprise generally hexagonal shaped segments. In an embodiment the electrode segments comprise generally square shaped segments.

In an embodiment, a pattern of any number (n) of electrode segments can be used. One example of a practical value of n is 30. In practice any range of n between approximately 16 and approximately 1024 may be useful. An exemplary value of n is 256. This number of electrode segments may be cost effective and provide adequate resolution. Larger values of n provide more accurate imaging of the electrode current distribution and may be useful for wood lengths with large cross-sectional area. However, for a given overall electrode area, as n increases effective electrode area reduces and cost increases.

In an embodiment the substantially circular flat face of the first electrode assembly 104 is adapted to contact the first end of the log 110. The n electrode segments collectively form the circular flat face of the electrode assembly 104.

In an embodiment the face of the assembly 104 is larger than the expected diameter of the log 110. For many timber species virtually no current flows in a heartwood portion of the log 110. No current flows between those portions of the electrode assemblies 104 and 106 that do not contact the log 110. In an embodiment the distribution of current within the log 110 is used by the controller 112 to infer one or more of the diameter of the log 110, the heartwood dimensions of the log 110, the sapwood dimensions of the log 110.

In an embodiment the shape of the flat face of the first electrode assembly 104 is generally circular. In an embodiment the shape of the flat face is hexagonal. In an embodiment the first electrode assembly 104 comprises tessellating, or otherwise juxtaposed, electrode segments of any shape and size.

In an embodiment two or more of the electrode segments include an individual electrical connection to the electric power source 108. In an embodiment each of the electrode segments includes an individual electrical connection to the electric power source 108. The controller 112 monitors the current flowing through individual segments. In an embodiment the segments of electrode assembly 104 are embedded in an epoxy bed adapted to provide electrical isolation between each electrode segment.

In an embodiment the electrode segments are mounted using one or more of GRP (fibreglass), thermoplastic, thermosetting plastic, ceramic, glass, porcelain, phenolic resin composite, any other suitable composite.

Figure 3:
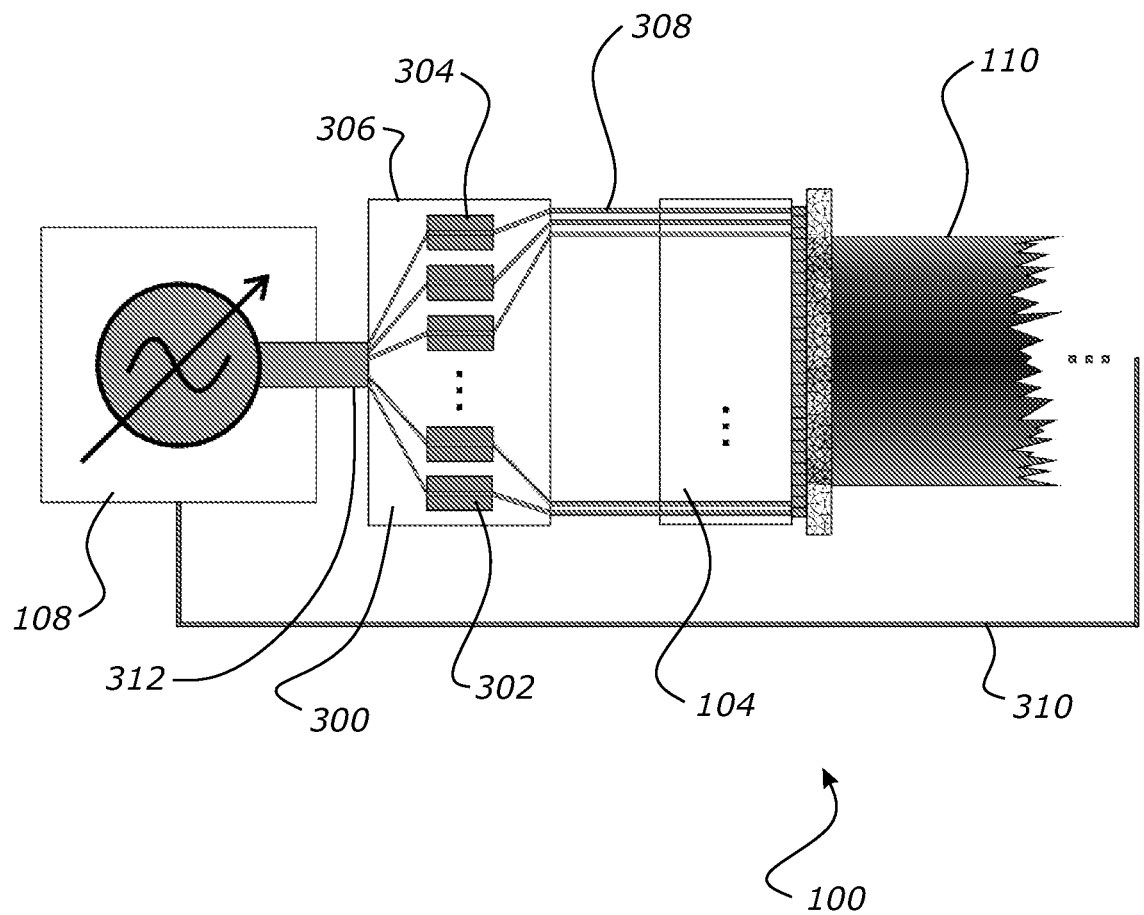
FIG. 3 shows an embodiment of the wood heating system of FIG. 1 adapted to connect and disconnect electric power flow.

FIG. 3 shows an embodiment of the wood heating system 100 adapted to connect and disconnect electric power flow between the electric power source 108 and the first electrode assembly 104.

In an embodiment the system 100 includes a distribution component 300 interposed between the power source 108 and the electrode assembly 104. The distribution component 300 comprises at least one printed circuit board assembly (PCBA). Examples of PCBAs are shown at 302 and 304 respectively. At least some of the PCBAs are positioned within a housing 306.

In an embodiment at least some of the PCBAs within the distribution component 300 are paired to respective electrode segments within the electrode assembly 104. Individual PCBAs are connected to respective electrode segments via a plurality of electrical lines indicated generally at 308.

A return path 310 connects the electric power source 108 to the second electrode assembly (not shown) that is in contact with the second the end of the log 110.

In an embodiment, each electrode segment is connected to an individual control PCBA 302 and 304. The PCBAs are in turn assembled onto a motherboard (MB) that has individual electrical connections to each electrode segment within electrode assembly 104. A high voltage cable 312 supplies a common electrical connection to the mother board, which is routed to carry excitation current to each of the PCBAs.

In an alternative embodiment each PCBA comprises a current sensor. The output of each PCBA's current sensor is fed to the MB. The outputs of all PCBAs (which may be multiplexed) are fed to a common multi-channel Analogue to Digital Converter (ADC) connected to, or integrated with, a microcontroller (uC) or other Programmable Logic Device (PLD) on the MB. The uC or PLD repeatedly transmits an array of data, representing the present value of current in each segment, to a suitable receiver connected to a Supervisory Control and Data Acquisition System (SCADA) using means such as optical fibre or wireless data transmission. In an embodiment the small amount of power (for instance in the range of 1 to 10 W) needed by the sensors, ADC, uC or PLD and optical fibre or wireless transmitter is harvested from the Joule heating current flowing through the electrode.

In an embodiment the PCBAs comprise one or more of a bilateral switch adapted to block AC voltage, a current sensor, a voltage sensor, signal conditioning electronic circuitry. In an embodiment the PCBAs each have connected a first optical fibre and a second optical fibre. The first optical fibre comprises an optical input which, when energised, opens the bilateral switch which is closed by default, thereby disconnecting the relevant electrode segment. The second optical fibre is an optical output that produces a train of pulses of frequency proportional to the current through the relevant segment if the switch is closed, or voltage across the relevant switch if the switch is open. The current and voltage are thereby monitored at the electrode assembly itself.

In an embodiment the bilateral switches are typically capable of blocking voltages up to about 600 Vrms, but cannot necessarily sustain full system voltage. It is desirable that each switch closes itself if the instantaneous voltage across it exceeds a certain value. It is also desirable that at least one switch on each electrode is always left closed.

In an embodiment the switch elements are Depletion-Mode Field Effect Transistors (DMFETs) that are normally closed. In an embodiment the DMFETs comprise junction FETs (JFETs) or metal-oxide-semiconductor FETs (MOS-FETs). In an embodiment the switch elements comprise silicon MOSFETs. In an embodiment the switch elements comprise silicon carbide JFETs.

In an embodiment the controller 112 from FIG. 1 is adapted to open and close electrode segments in sequence. This in turn has potential to provide information about the contact resistance of one or more of the electrode segments, to ensure good electrical contact with the log 110 and/or information about current flow within the log 110.

In an embodiment one or more of the PCBAs is provided with a local electric power source. One or more of the PCBAs in the first electrode assembly 104 may be subjected to high voltages relative to ground. In an embodiment, the electrode segments within the electrode assembly 104 do not all have the same voltage as each other, especially when one or more segments' switches are open. Therefore, an electric power source with high isolation from ground and much smaller isolation requirements from its neighbours is desirable for each individual PCBA 302, 304.

In an embodiment, individual PCBAs consume approximately 25 mW (5V at 5 mA) each, meaning less than 1 W is required for an embodiment of the electrode assembly 104 that includes 30 electrode segments.

In an embodiment high isolation is provided by one or more of a remote LED array powering an internal PV panel, an optical supply through free air or via light-pipe powering an internal PV panel, an internal compressed air-driven electrical generator supplied via electrically insulating air pipe, a rechargeable battery. In an embodiment a common high-isolated supply, isolated to the order of approximately 20 kVrms from ground potential, is fed to each PCBA from a common connection on the motherboard. In an embodiment each PCBA comprises a local isolated DC-DC converter to provide inter-segment isolation in the order of 500 Vrms.

Figure 4:
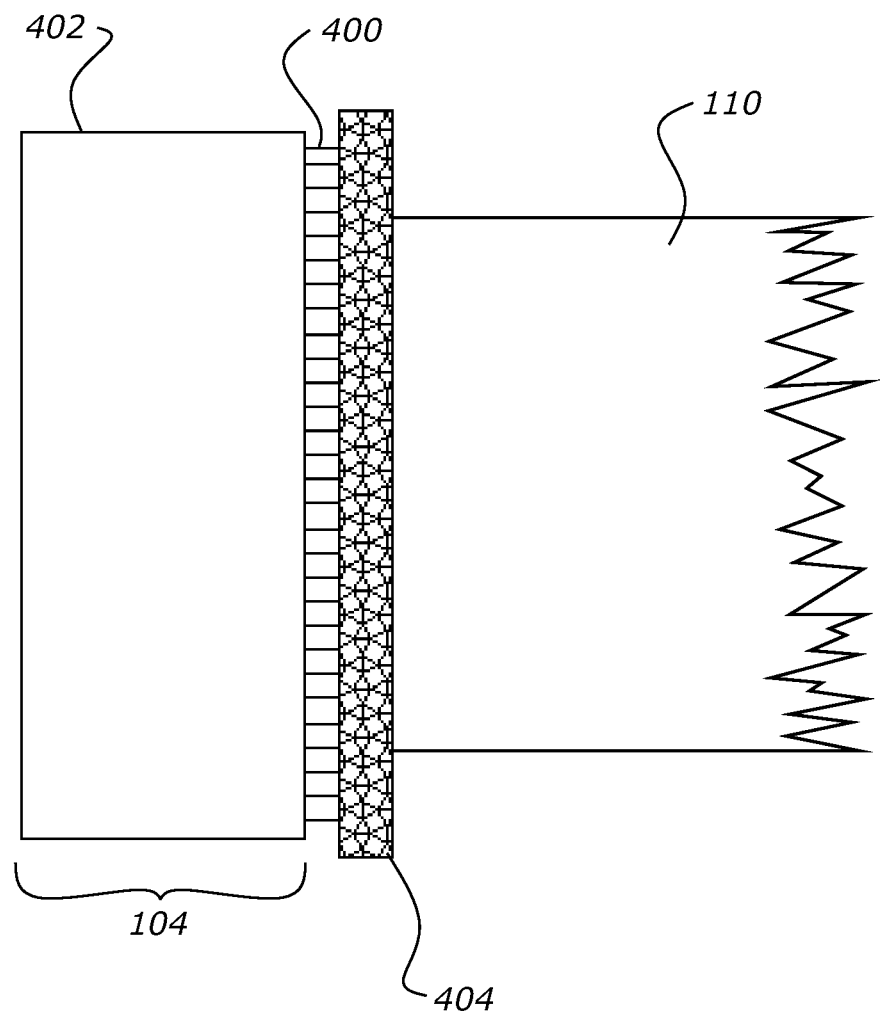
FIG. 4 shows an embodiment of the wood heating system of FIG. 1 adapted to ensure a good connection between an electrode assembly and a log.

FIG. 4 shows an embodiment of the wood heating system 100 adapted to ensure a good connection between the first electrode assembly 104 and the log 110. In an embodiment the first electrode assembly 104 includes a plurality of electrode segments 400 extending from within a housing 402. The electrode segments 400 terminate in a substantially flat face.

In an embodiment the system 100 includes a compressible medium interposable between the flat face of the electrode assembly 104 and a first end of the log 110. In an embodiment the compressible medium comprises a porous structural pad. One example shown in FIG. 4 is an open-cell foam pad 404.

In an embodiment the pad 404 is electrically conductive to enable current flow from the electrode segments 400 through the pad 404 to the first end of the log 110. In an embodiment the pad is wetted with a conducting gel to an extent sufficient to ensure electrical conductivity of the pad 404. In an embodiment the pad is saturated with the conducting gel.

In an embodiment the pad 404 is not electrically conductive, relying solely on the gel for electrical conductivity. In an embodiment the pad 404 is permeable in all directions. In an embodiment the pad 404 is permeable only in an axial direction.

In an embodiment the pad 404 is formed so as to provide conformable contact between the substantially flat face of the electrode assembly 104 and the first end of the log 110 which may comprise an uneven end-grain wood fibre surface. The use of a compressible pad has the potential to enable suitably designed electrode assemblies to conform to any irregularities in the surface of the first end of the log 110.

Figure 5:
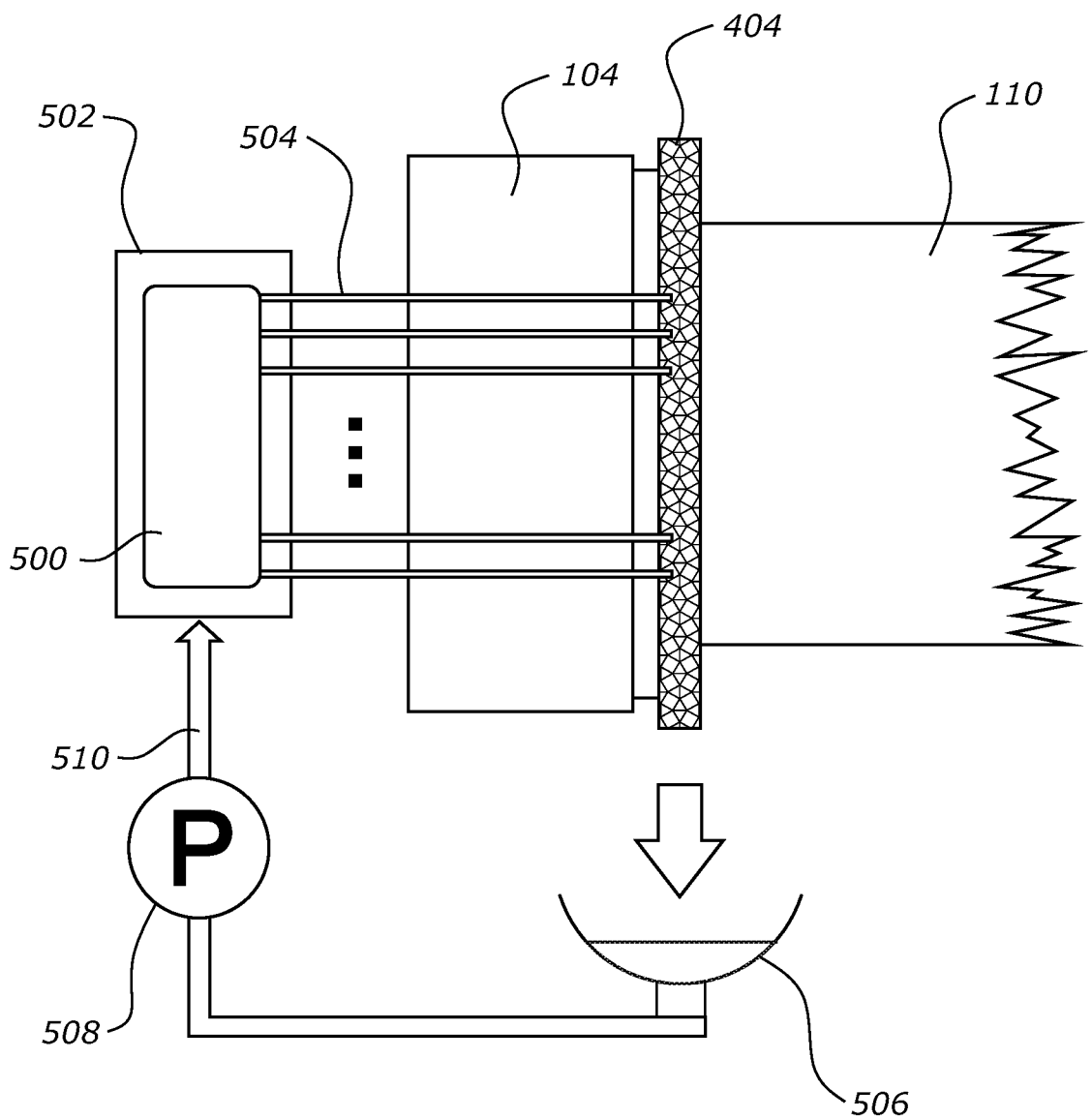
FIG. 5 shows an embodiment of the wood heating system of FIG. 1 adapted to maintain wetting of a pad.

FIG. 5 shows an embodiment of the wood heating system 100 adapted to maintain wetting of the pad 404. The conducting gel 500 is pumped through a manifold 502 that distributes the conducting gel via tubes 504 connecting the manifold 502 to the pad 404.

In an embodiment the pad 404 is saturated in order to make a good electrical connection. Excess gel 500 is allowed to drip down into a reservoir 506. The collected gel 500 is filtered and redistributed by a pump/filtration unit 508. The filtered gel is returned to the manifold 502 via a return tube 510.

In an embodiment the gel is maintained at high voltage. High-voltage operation may be enabled by employing a pneumatic pump rather than an electric pump. Furthermore, each of the components containing the conducting gel are kept at a certain distance from the ground to ensure electrical isolation. The compressed air supply to the pneumatic pump may be conducted through electrically isolated tubing with high voltage withstand capability.

In an embodiment the pad 404 is applied to a first end of the log 110 using a pneumatic ram, hydraulic ram, or compression spring, acting on the electrode assembly 104.

In an embodiment the ram or spring acting on the pad exerts a pressure of typically 2 to 20 kPa on the log end.

In an embodiment the pneumatic or hydraulic rams are fitted with position sensors, from which the controller 112 can determine log length.

In an embodiment the electrode assembly 104 is shaped to provide a conductive surface parallel to the first end of the log 110. In circumstances where the first end of the log 110 has not been cut perpendicular to an axis of the log 110, an electrode assembly surface can be made parallel to the first end of the log using Cardan joints between for example an actuating ram and a housing of the electrode assembly 104.

In an embodiment the electrically conductive gel has the potential to fill small gaps between the pad 404 and the fibres in the first end of the log 110. This includes filling up the end grain fibres of the log 110 that are likely to dry out after harvest.

In an embodiment the gel is formed with a suitable viscosity other than a liquid to minimise dripping under the effects of gravity and/or minimising the opening up of voids.

In an embodiment the gel is applied to the electrode assembly 104 under hydraulic pressure to ensure that voids are filled and/or to prevent drying out during operation of the wood heating system 100. In an embodiment this is achieved by pumping gel through the manifold 502 via the tubes 504 through the substantially flat face of the electrode assembly 104 to the pad 404.

In an alternative embodiment, the wetting system comprises an electrically conductive fluid-filled tank into which the compressible medium, detached from the electrode and held in a suitable frame, is immersed, using a suitable actuator. The compressible medium is compressed (e.g. by a pneumatic actuator), expelling any air, and then released, taking up a full load of fluid. The framed compressible medium is then lifted from the tank, by the actuator, into position between the electrode assembly and the log end.

In an embodiment the electrically conductive gel 500 includes an aqueous sodium chloride solution sufficient to provide suitable electrical properties. In an embodiment, the sodium chloride solution is saturated. In an embodiment the conductive gel 500 includes a sodium chloride solution of about 0.16 grams/litre. In an embodiment the conductive gel 500 includes a solution with an electrical conductivity of about 0.01 to 0.1 siemens per metre at 20° C. In an embodiment, the electrically conductive gel 500 has an electrical conductivity of 0.03 siemens per metre at 20° C. An electrical conductivity of 0.03 siemens per metre at 20° C. has been found to be particularly suitable when the system is used to heat *Pinus radiata* logs.

In an embodiment the gel is at least as electrically conductive as the most conductive region of the wood in the axial direction. For *Pinus radiata* there are only two regions: sapwood and heartwood. The sapwood region is the most conductive.

In an embodiment the electrically conductive gel 500 includes a gelling agent. In an embodiment the gelling agent comprises *psyllium* husk. In an embodiment the gelling agent comprises sodium carboxymethyl cellulose (microcrystalline cellulose). In an embodiment the gelling agent provides sufficient conductivity without the addition of any salt.

In an embodiment the electrically conductive gel 500 comprises deionized water with the addition of 0.16 grams/litre of sodium chloride and 21 grams per litre of *psyllium* husk.

In an embodiment the electrically conductive gel 500 comprises another chemical salt solution and *psyllium* husk.

In an embodiment the electrically conductive gel 500 comprises only water and *psyllium* husk.

In an embodiment the electrically conductive gel 500 may be pre-heated. Pre-heating may enhance initial contact conductivity and/or ensure ends of the wood length get hot, despite the heat-sinking effect of the electrode segments.

Figure 6:
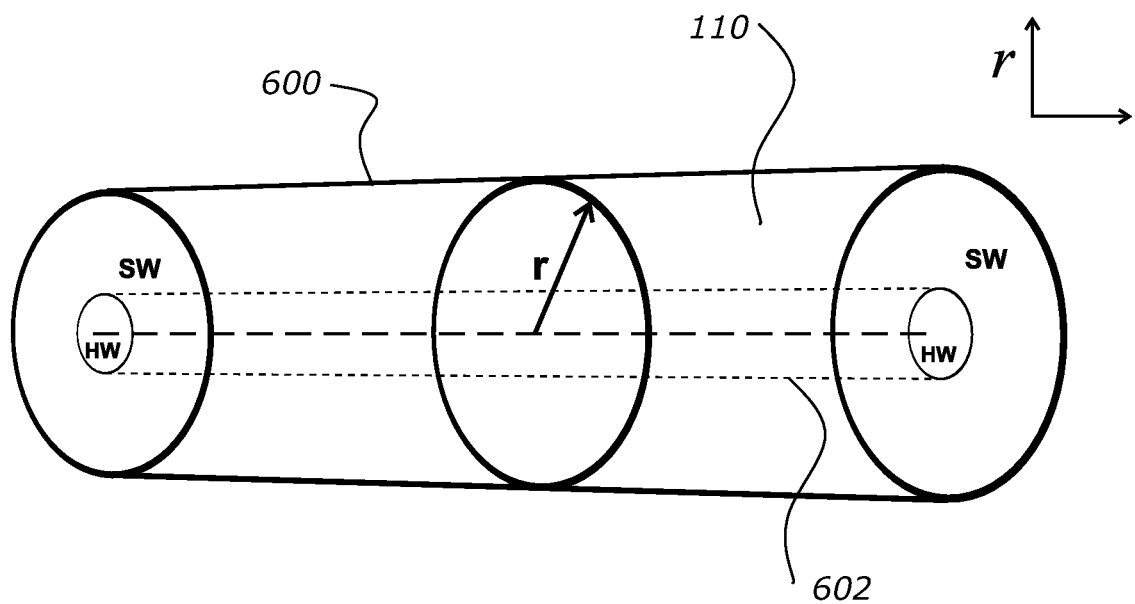
FIG. 6 shows an example of geometry used to determine how much energy the wood heating system of FIG. 1 is required to apply to a log.

FIG. 6 shows an example of geometry used to determine how much energy the wood heating system 100 is required to apply to a log 110. The geometry for the calculations described below approximates a log 110 as two or more tapered generally cylindrical (or conic section) volumes.

In an embodiment a first tapered cylinder 600 represents a log 110. The tapered cylinder 600 has a small end diameter smaller than a large end diameter.

In an embodiment a second tapered cylinder 602 represents a heartwood region of the log 110. The tapered cylinder 602 usually has a small end diameter smaller than a large end diameter.

In an embodiment the tapered cylinder 600 shares a common axis with the tapered cylinder 602. In an embodiment the tapered cylinder 602 is smaller in diameter along its length than the tapered cylinder 600. In an embodiment the sapwood region is defined as a function of cylinder 600 and cylinder 602. For example a sapwood region volume can be calculated as the volume of cylinder 600 less the volume of cylinder 602.

The sapwood region within the log 110 contains electrically conducting ions. It is generally within the sapwood region that most of the Joule-heating process takes place. The heartwood region is assumed to be electrically non-conducting in some species, including *Pinus radiata*. In some species there may be some electrical conduction in the heartwood region. In some species there may be a transition or dry zone between the heartwood region and the sapwood region.

Figure 7:
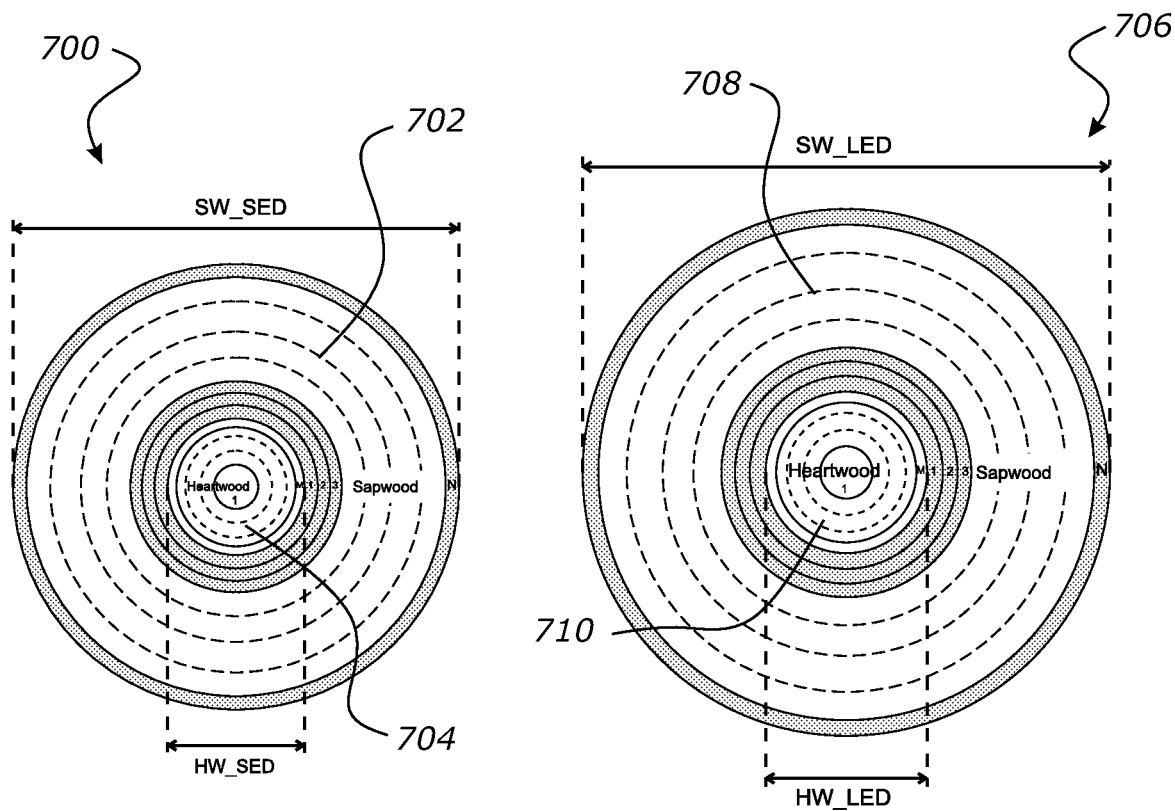
FIG. 7 shows first and second cross-sections of a log.

FIG. 7 shows a first cross-section 700 of a small end of log 110. The cross-section 700 shows the sapwood region 702 and the heartwood region 704 further divided into a plurality of concentric cylindrical or conical control volumes. In an embodiment each volume represents a notional thin uniform layer in the log 110. The control volumes are represented by a series of points or nodes along a calculated radius of the log 110.

FIG. 7 also shows a second cross-section 706 of a large end of log 110. The second cross-section 706 shows the sapwood region 708 and the heartwood region 710 further divided in to a plurality of concentric cylindrical or conical control volumes.

In an embodiment, an electro-thermal model is used to determine how much energy to inject into the log 110 and a constant power (P) in order for it to reach a predefined temperature. A typical log comprises a central pith surrounded by a heartwood portion. The heartwood portion is itself surrounded by a sapwood portion. Typically the sapwood portion is covered with bark. The heartwood region typically comprises dead cells which have different electrical and thermal properties to the sapwood. The heartwood region is completely absent in some young trees and/or top logs of older trees. In some species, such as *Pinus radiata*, the heartwood region has significantly different electrical and thermal properties to the sapwood.

Figure 8:
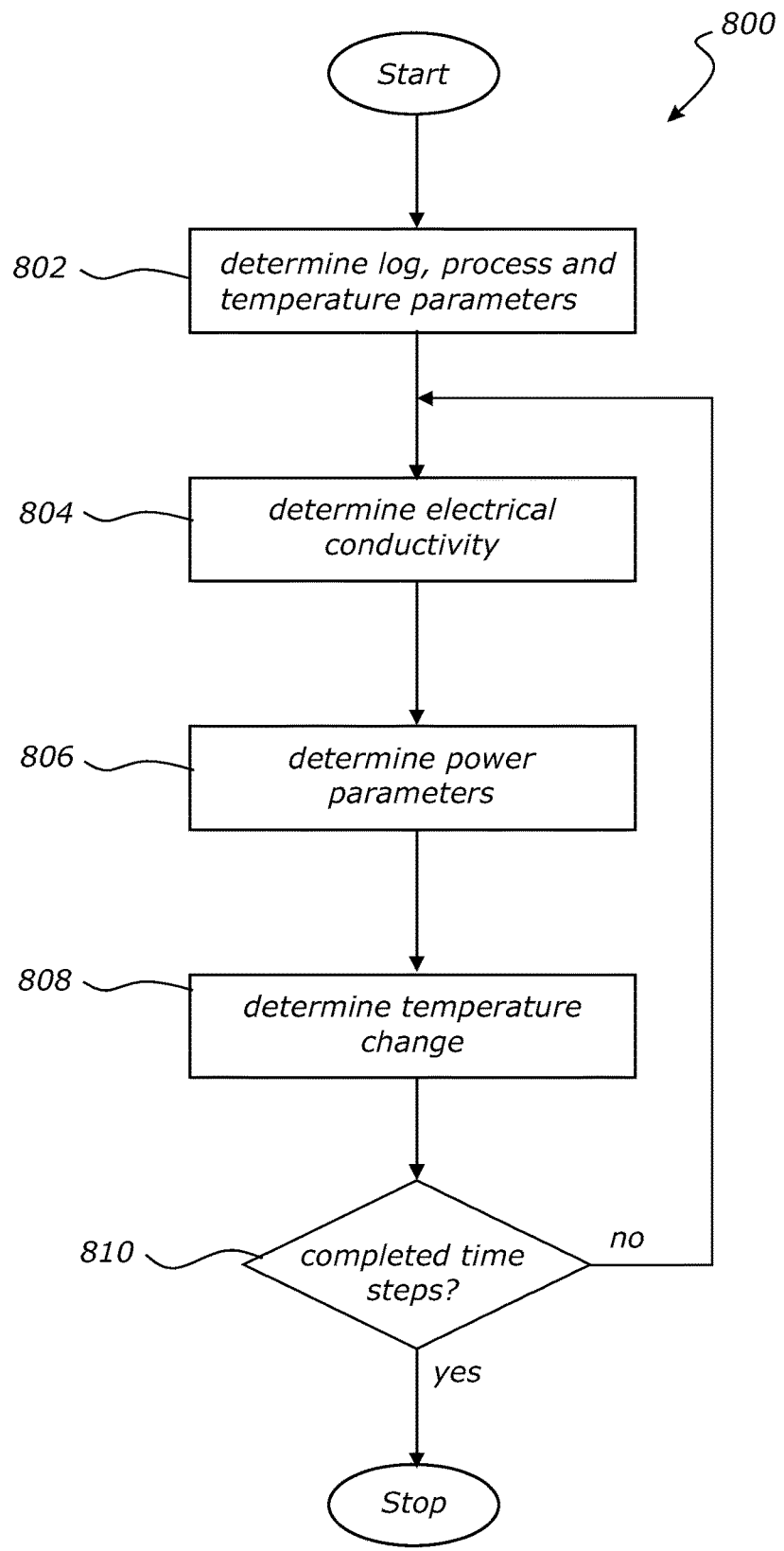
FIG. 8 shows an example of a method of determining the energy to be applied to a log.

FIG. 8 shows an example of a method 800 of determining the energy to be applied to a log. One step includes determining 802 log parameters. In an embodiment the log parameters include log dimensions. In an embodiment the log dimensions include one or more of a large end diameter (LED), a small end diameter (SED), a heartwood diameter at the large end ($LED_{HW}$), a heartwood diameter at the small end ($SED_{HW}$), a length of the log (L).

In an embodiment one or more of LED, SED, $LED_{HW}$, $SED_{HW}$ values are measured optically using pattern recognition. In an embodiment LED, SED, $LED_{HW}$, $SED_{HW}$ values are inferred from electrode segment current distribution. In an embodiment L values are measured by electrode position sensors. Examples include a potentiometer or linear variable differential transformer (LVDT).

In an embodiment, the log parameters include a volume (V) of the log which is calculated as:

$$V = \frac{\pi L}{12}(SED^2 + SED*LED + LED^2)$$

Where V is the volume of the log in m³, and L is the length of the log in m.

In an embodiment, the log parameters include a heartwood volume ($V_{HW}$) of the log which is calculated as:

$$V_{HW} = \frac{\pi L}{12}(SED_{HW}^2 + SED_{HW}*LED_{HW} + LED_{HW}^2)$$

In an embodiment, the log parameters include a sapwood volume ($V_{SW}$) of the log which is calculated as:

$$V_{SW} = V - V_{HW}$$

In an embodiment the log parameters include one of more of a sapwood moisture content ($MC_{SW}$), a sapwood basic density ($BD_{SW}$), a heartwood moisture content ($MC_{HW}$), a heartwood basic density ($BD_{HW}$), a log mass (m), a sapwood mass ($m_{SW}$), a heartwood mass ($m_{HW}$), equation(s) defining axial electrical conductivity of timber ($\sigma$) as a function of temperature.

Some timber species have more than two wood regions. For instance *Sequoia sempervirens* (coast redwood) has three distinct regions, each with differing MC, BD and electrical conductivity. In an embodiment three or more regions may be incorporated into the method, each with its own set of control volumes.

In an embodiment the moisture content is represented as a ratio between a mass of water in the log and the mass of dry wood in the log. For example, if the water in the log weighs 1.5 times as much as the dry wood, the moisture content would be approximately 150%, or 1.5 kg$^{-1}$ In an embodiment an m value is measured directly for example by load cell. In an embodiment $BD_{SW}$ and $BD_{HW}$ values are estimated from typical data for forest provenance.

In an embodiment, $MC_{SW}$ and $MC_{HW}$ values (in kgkg$^{-1}$) are calculated to agree with observed mass to volume ratio. For example, $MC_{SW}$ and $MC_{HW}$ may be calculated as follows:

$$MC_{SW} = \frac{m_{SW}}{V_{SW}*BD_{SW}} - 1$$

$$MC_{HW} = \frac{m_{HW}}{V_{HW}*BD_{HW}} - 1$$

In an embodiment, the mass of the sapwood portion ($m_{SW}$) is calculated from the estimated moisture content ($MC_{SW}$) and basic density ($BD_{SW}$) of the sapwood portion. For example, $m_{SW}$ may be calculated as follows:

$$m_{SW} = V_{SW}*BD_{SW}(1+MC_{SW})$$

In an embodiment, the mass of the heartwood portion ($m_{HW}$) is calculated from the estimated moisture content ($MC_{HW}$) and basic density ($BD_{HW}$) of the heartwood portion. For example, $m_{HW}$ may be calculated as follows:

$$m_{HW} = V_{HW}*BD_{HW}(1+MC_{HW})$$

In an embodiment, the mass of either the heartwood or sapwood portion is derived from the following equation:

$$m = m_{SW} + m_{SW}$$

It will be appreciated that as it is only possible to measure the total mass of the log (m), it is necessary to estimate at least the basic density and moisture content of either the heartwood or the sapwood to determine the relative masses of the heartwood ($m_{HW}$) and sapwood ($m_{SW}$) portions.

In an embodiment, the parameters are calculated as follows using the applicable equations defined above: measure m, LED, SED, $LED_{HW}$, $SED_{HW}$; calculate $V_{HW}$, $V_{SW}$; estimate $MC_{HW}$, $BD_{HW}$; calculate $m_{HW}$; calculate $m_{SW}$ using $m_{SW} = m - m_{HW}$; estimate $BD_{SW}$; calculate $MC_{SW}$. This embodiment would be suitable for a *Pinus radiata* log, for example.

In a *Pinus radiata* log, for example, the electrical conductivity of a sapwood region is typically several orders of magnitude higher than that of a heartwood region within the same log. Therefore substantially all the electric current flows in the sapwood. It is therefore within the sapwood region that heat is primarily generated.

Step 802 of the method includes determining process parameters. In an embodiment the process parameters include a machine power (P) representing the amount of power the log heating system 100 is configured to apply to the log 110.

In an embodiment the log heating system 100 is configured to supply constant power to the log 110 over the full range of log resistance.

Supplying total energy to a log 110 in a single long excitation tends to cause formation of hot and cold spots inside the log due to non-uniformities such as knots and resin pockets. In an embodiment a long excitation period is split into a plurality of shorter excitation periods, separated by relaxation intervals. The duration of each excitation period is defined by the amount of energy (Q) introduced during the excitation period. The value of Q in each excitation may be the same, or different.

Relaxation intervals between excitations permit hot and cold spots within a log to equilibrate during the relaxation intervals. Relaxation intervals have the potential to decrease the temperature difference between hot spots and cold spots within the log. The relaxation intervals are defined as periods of time. The duration of the relaxation interval between successive excitations may be the same, or different.

In an embodiment the process parameters include one or more of a predefined relaxation interval duration, two or more different predefined relaxation interval durations, a predefined number of relaxation intervals, a predefined excitation energy value (Q), two or more different predefined excitation energy values ($Q_1$, $Q_2$ etc.), and a predefined number of excitation periods.

Step 802 of the method includes determining temperature parameters associated to the log. In an embodiment the temperature parameters include a chamber temperature representing the temperature of the air surrounding the log. The chamber temperature affects the transfer of heat between the log and the air.

In an embodiment the temperature parameters include an initial bulk log temperature ($T_i$). $T_i$ can be determined directly, e.g. by inserting at least one temperature sensor into at least one end of the log.

In an embodiment at least one temperature sensor is incorporated into at least one of the electrode assemblies, allowing initial and/or continuing real-time temperature measurement in at least one location at/in at least one end of the log.

Alternatively $T_i$ can be estimated by calculating an equilibrium temperature equal to the average ambient temperature over a predefined historical period, for example a previous day or a previous two days.

In an embodiment the initial log surface temperature is deliberately reconditioned to a temperature higher or lower than $T_i$.

In an embodiment the temperature parameters include a target temperature $T_t$ of the log. The target temperature may be different for different applications. Within each application, the target temperature may necessarily be different for individual industry requirements. For example, different varieties of logs may require different working temperatures in a log peeling application. Also, for example, various jurisdictions may have different temperature requirements for phytosanitary treatment based on the species of insects that require destruction.

A minimum temperature for phytosanitary treatment is typically at least approximately 56° C., for example 60° C. A log will typically have a core temperature in the range of 10° C. to 20° C. or cooler meaning that a log placed in a heated chamber begins the log heating process with the outer wood hotter than the inner wood.

In an embodiment, where the temperature parameters include $T_t$ and $T_i$, the process parameters include a total energy ($Q_T$) calculated as:

$$Q_T = (m_{SW}C_{pSW} + m_{HW}C_{pHW})(T_t - T_i)$$

where $C_p$sw and $C_{pHW}$ are specific heat capacity of sapwood and heartwood respectively. If there are more timber regions in the species being heated, a similar term can be added for each region.

In an embodiment representative of phytosanitary treatment of *Pinus radiata*, where the temperature parameters include $T_t$ and $T_i$, total energy ($Q_T$) can be approximated by:

$$Q_T = m_{SW}C_{pSW}(T_t - T_i)$$

In an embodiment the process parameters include the energy of a single short excitation (Q) calculated as:

$$Q = \frac{Q_T}{N_{exc}}$$

where $N_{exc}$ is the number of excitations.

In an embodiment the process parameters include the time ($t_{exc}$) required to supply the amount of energy (Q) in a single excitation, calculated as:

$$t_{exc} = \frac{Q}{P}$$

where P is the electrical power.

In an embodiment the process parameters include a number (N) of control volumes in a sapwood region of the log. The process parameters may also include a number of control volumes in a heartwood region of the log.

A further step determines 804 an electrical conductivity ($\sigma$) of the timber within each of the sapwood control volumes 1 to N, with respect to a current temperature of the control volume. In an embodiment a value for $\sigma$ is based on a statistically derived equation specific to *Pinus radiata*. In an embodiment, $\sigma$ is calculated as follows:

$$\sigma = \alpha \cdot e^{\left[-2.60 + 0.017(T-55) - 0.073\frac{(T-55)^2}{1000}\right]}$$

where T is temperature in ° C. and $\alpha$ is a multiplication coefficient for electrical conductivity.

It will be appreciated that different equations for $\sigma$ are appropriate for different timber species. In an embodiment a lookup table provides equations and values for $\sigma$ for different timber species.

A further step determines 806 power parameters associated to the log.

In an embodiment the power parameters include a resistance of each of the sapwood control volumes ($R_1$ to $R_N$) based at least partly on the electrical conductivity calculated at step 804 and the dimensions of the control volume.

In an embodiment the power parameters include a total resistance of the log ($R_T$), which is the parallel combination of $R_1$ to $R_N$ determined above, as follows:

$$\frac{1}{R_T} = \frac{1}{R_1} + \frac{1}{R_2} + \ldots + \frac{1}{R_N}$$

In an embodiment the power parameters include a voltage (U) across the log. Given the application of constant power (P) to the log, using the equation for power dissipation in a resistor, the value of U is calculated as:

$$U = \sqrt{PR_T}$$

In an embodiment the power parameters include a current (I) flowing through the log. Using Ohm's law, the value of I is calculated as:

$$I = \frac{P}{U} = \frac{U}{R_T}$$

In an embodiment the power parameters include a power dissipation density (S) in each of the sapwood control volumes calculated as follows:

$$S = \sigma \left(\frac{U}{L}\right)^2$$

A further step determines 808 a temperature change in each control volume by solving a 1-dimensional energy conservation equation:

$$\frac{\partial \rho C_p T}{\partial t} = \frac{\partial}{\partial r}\left(k \frac{\partial T}{\partial r}\right) + S$$

where $\rho$ is the green density and k is the thermal conductivity of the unseasoned wood, r is the distance from the log's central axis along a radius of the log and t is time. The source term S is always zero in heartwood control volumes in the case of *Pinus radiata*. Control volume temperature can increase or decrease.

The number of time-steps completed for each excitation period and relaxation interval is checked 810 against the predefined desired number of time-steps. If the desired number of time-steps has not yet been reached then steps 804, 806, 808 and 810 are repeated.

In an embodiment the number of time-steps and the number of control volumes are parameters defined for a particular model.

The electrical conductivity at step 804 is calculated using the new temperature determined at step 808.

In an embodiment, on completion of the method, plots of current and/or resistance versus time are produced for each excitation. In an embodiment radial temperature profiles at the completion of each excitation period and relaxation interval are plotted. In an embodiment transient temperature values for at least one value of r along a radius of the log, or for at least one depth below the log's surface are plotted.

In an embodiment the $R_T$ and I values determined in step 806 are compared directly in real-time, or near real-time, with values measured during the process. This real-time comparison has the potential to provide model validation and feedback for process control.

In an embodiment the control system applies the energy excitation periods and relaxation intervals determined by the method. In an embodiment the control system measures the total resistance of the wood length in real-time during the excitation periods. In an embodiment the control system verifies that the total resistance versus time varies according to the results of the method within a predefined tolerance. A suitable predefined tolerance may be 10% of absolute value.

In an embodiment the control system further measures the current density in, and/or resistance of, at least one control volume, or set of control volumes, during the excitation periods. In an embodiment the control system verifies that the current density and/or resistance of at least one control volume, or set of control volumes, varies according to the results of the method within a predefined tolerance. A suitable predefined tolerance may be 10% of absolute value.

In an embodiment, all input and calculated output parameters from the model are stored to a unique file for each log heated.

In an embodiment, all measured electrical and physical parameters are stored to a unique file for each log heated.

Figure 9:
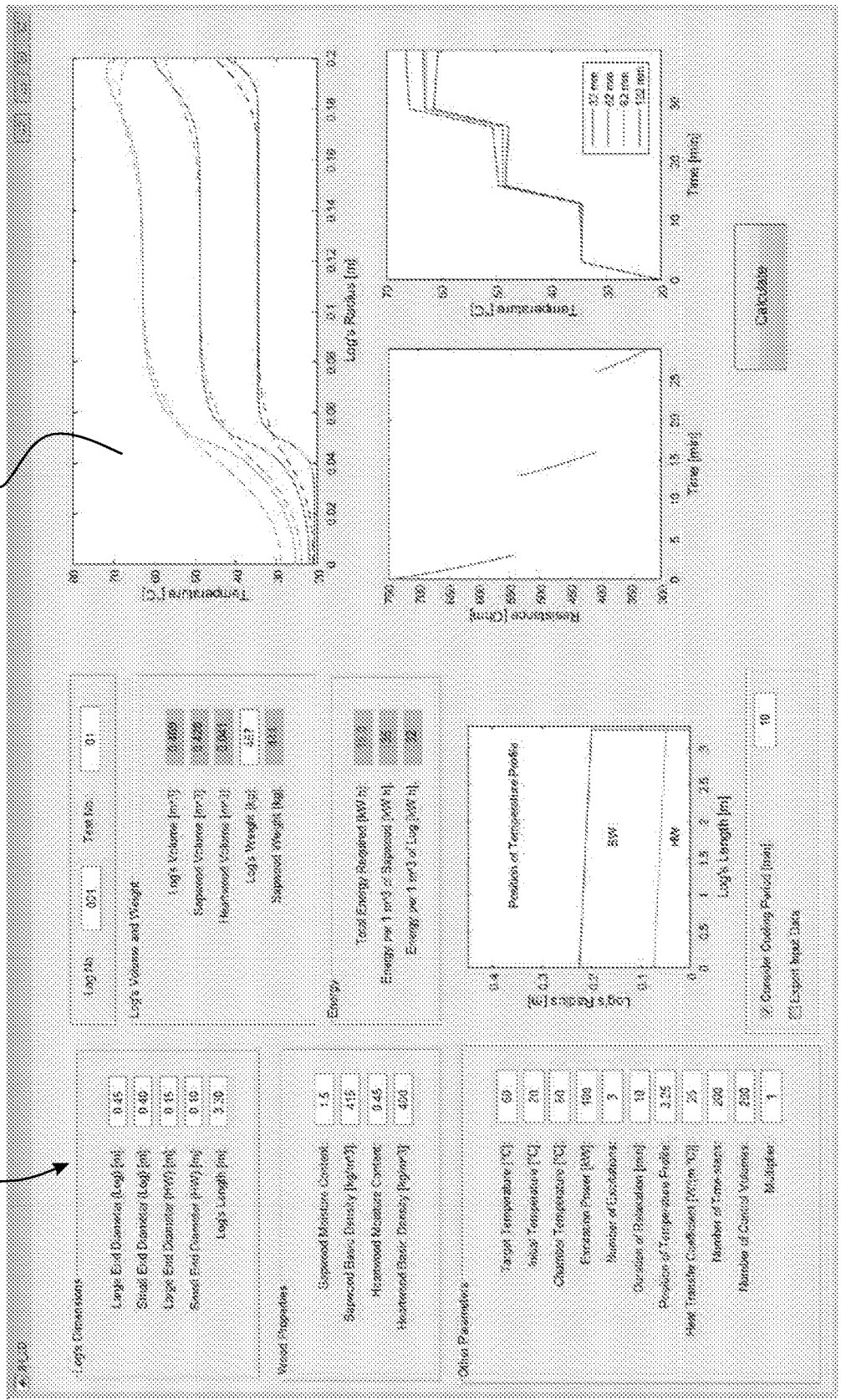
FIG. 9 shows an example of a graphical user interface (GUI) configured to receive data and to present output plots adapted for phytosanitary treatment of a log to a target temperature profile.

FIG. 9 shows an example of a graphical user interface (GUI) configured to receive data and to present output plots. The GUI 900 is adapted for phytosanitary treatment to a target of 60° C. The chamber temperature is set at 60° C. A representative temperature profile of a log having an initial temperature of 20° C. is indicated at 902.

Figure 10:
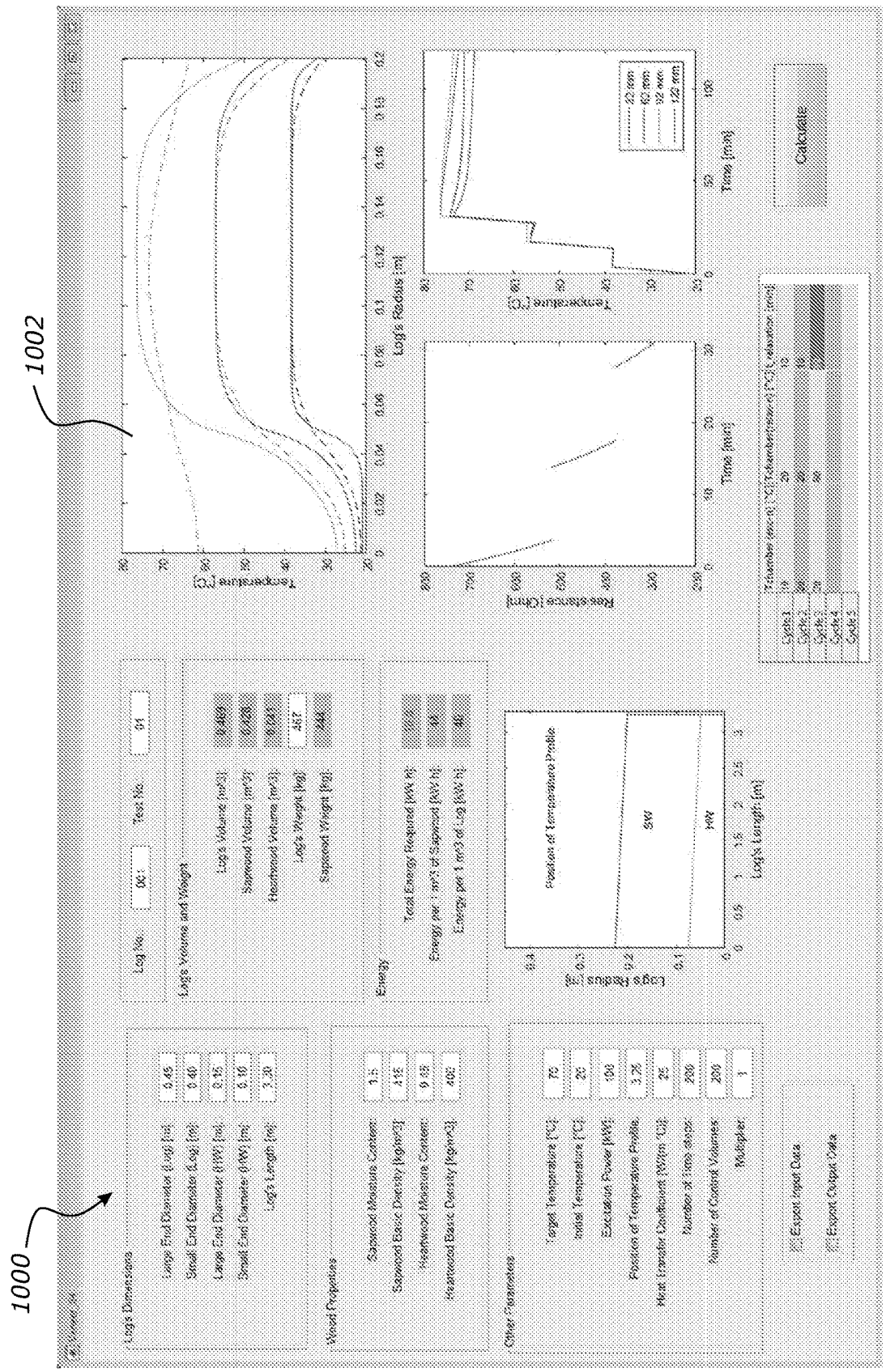
FIG. 10 shows an example of a GUI adapted for veneer peeling to a target temperature profile.

FIG. 10 shows an example of a GUI 1000 adapted for veneer peeling to a target of 70° C. The chamber is initially chilled to 10° C. A representative temperature profile of a log having an initial temperature of 20° C. is indicated at 1002.

The veneer peeling process shown in FIG. 10 has three excitation periods that alternate with three relaxation intervals. During each excitation, one third of the total energy is introduced to the log. The chamber is heated to 10° C. for the first excitation period. The chamber is heated to 20° C. for the second and third excitation periods. The three relaxation intervals have different temperatures and durations. The chamber is heated to 20° C. for the first and second relaxation intervals, and the first and second relaxation intervals have a duration of 10 minutes. The chamber is heated to 60° C. for the third relaxation interval, and the third relaxation interval has a duration of 90 minutes. Temperature profile 902 is markedly different from temperature profile 1002 even though the log has the same initial temperature of 20° C. This is because the initial difference between the temperatures of the inside and outside of the sapwood region of the log leads to higher electrical conductivity of the hotter part. When power is applied, this initially hotter part experiences higher power and therefore heats faster than the cooler part.

In a *Pinus radiata* phytosanitary application having N sapwood control volumes, for example an outer control volume N is initially at nearly 60° C. while an innermost control volume 1 is at 20° C. In this example the outer control volume N is more conductive and heats preferentially.

In a *Pinus radiata* veneer peeling application having N sapwood control volumes, for example an outer control volume N is initially cooled to around 10° C. while an innermost control volume 1 is at 20° C. In this example the inner control volume 1 is more conductive and heats preferentially.

By changing the relative initial temperatures of the inner and outer control volumes, the heat profile can be deliberately adjusted.

Figure 11:
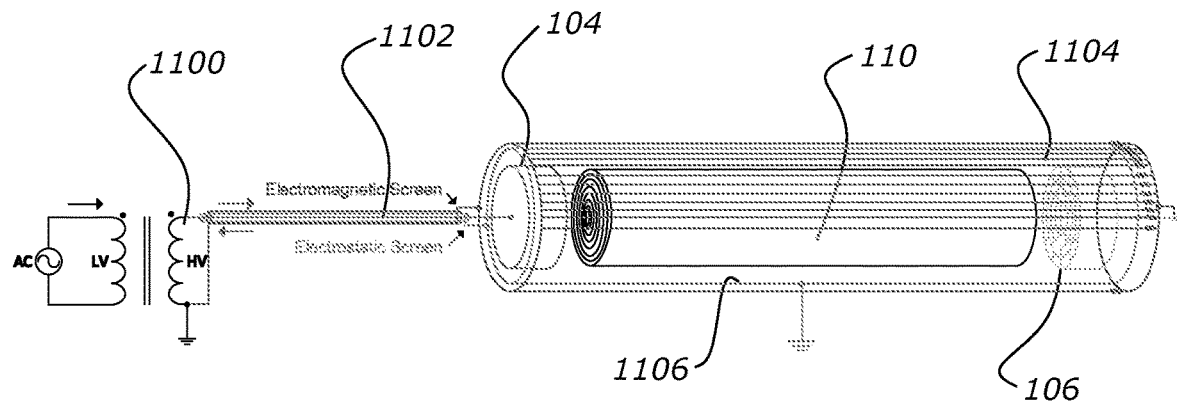
FIG. 11 shows an embodiment of the wood heating system of FIG. 1 that includes an electrostatic and/or electromagnetic screen/shield.

FIG. 11 shows an embodiment of the wood heating system 100 that includes an electrostatic and/or electromagnetic screen/shield.

In an embodiment when a log is undergoing Joule-heating, there is the potential for a substantial current of the order of 10 A to 50 A or more through the log. There is a further potential for a high voltage of the order of 10 kV to 50 kV or more across the log. If careful attention is not paid to the layout of the current path, considerable electric (E) and magnetic (H) fields will exist outside the log. This has the potential to lead to undesirable coupling with, and interference to, other equipment and processes in the vicinity. International standards define the allowable levels of emitted fields, such that non-complying products and processes can be identified.

In the embodiment shown in FIG. 11 a unipolar high voltage (HV) alternating current (AC) supply is applied to a log using a step-up transformer. Current flows from the HV winding of the transformer 1100 through the centre conductor of a coaxial or triaxial cable 1102, through first electrode assembly 104 and into the log 110. The current continues through the second electrode assembly 106 into an electromagnetic screen 1104, through which it returns coaxially to an earthed end of the HV winding 1100. This has the potential to cancel the magnetic field around the log 110 and cable 1102.

In an embodiment, the electromagnetic (EM) screen 1104 around the log 110 is a conducting cylinder at approximately ground potential. In an embodiment, in order to have evenly distributed current through the cylinder, to avoid current crowding, the cylinder is made up from a plurality of individual conductors with small series balancing impedances to balance the current in each conductor.

In an embodiment the EM screen 1104 also acts as an electrostatic (ES) screen. In this embodiment a coaxial cable is sufficient.

In an embodiment, a separate electrostatic (ES) screen 1106 is also employed, again coaxially, inside the EM screen 1104. The purpose of the ES screen is to return displacement currents, caused by alternating voltage on the log surface, directly to supply ground rather than allowing them to flow through the EM screen 1104. In this embodiment the cable must be triaxial, rather than coaxial.

Figure 12:
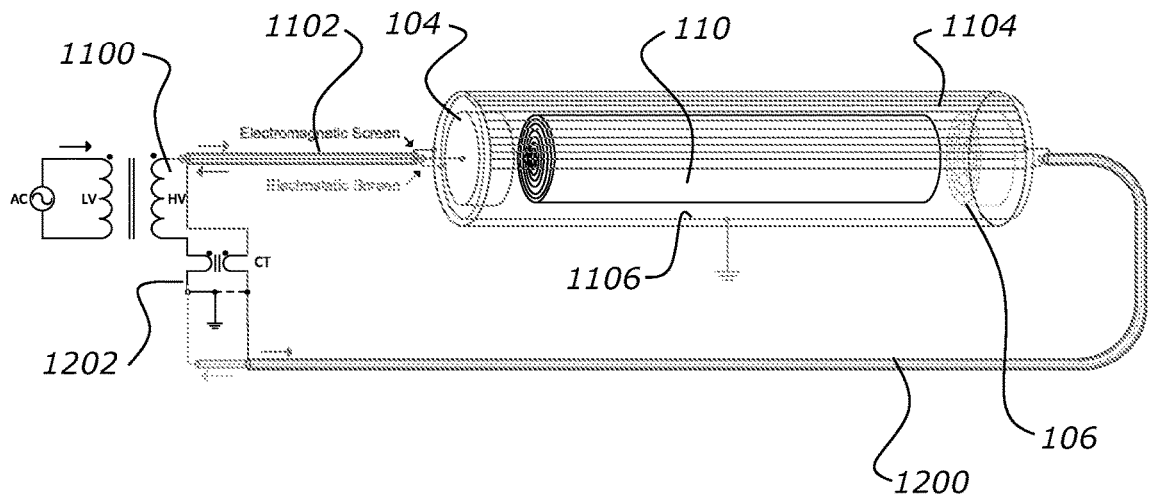
FIG. 12 shows an embodiment of the wood heating system of FIG. 1 in which the current in the electromagnetic screen is supplied by a winding of a current transformer.

FIG. 12 shows an embodiment of the wood heating system 100 in which the log power flows through the high voltage cable 1102 and first electrode assembly 104. The current passes through the log 110 and second electrode assembly 106. The current returns through a return cable 1200 to ground.

A primary winding of a current transformer (CT) 1202, with unity turns ratio, is placed in series with an earth end of the HV winding 1100. A secondary winding of the current transformer 1202, which may be earthed as shown, drives an exact replica of the log current around the EM screen 1104 to oppose the log current and cancel the external magnetic field.

In an embodiment, the CT 1202 supplies an approximate replica of the log current, to partially cancel the external magnetic field. The error difference between the log current and the partial cancellation current is measured, for example by a further CT, and is input to a servo amplifier which drives an additional appropriate nulling current around the EM screen 1104 to fully cancel the external magnetic field.

In an embodiment the current transformer 1202 is adapted to drive the burden impedance of the EM screen 1104, including any balancing impedances. In an embodiment an ES screen 1106 is employed in which case it is possible to permit the EM screen 1104 to float or be connected to any convenient potential, rather than being grounded.

Figure 13:
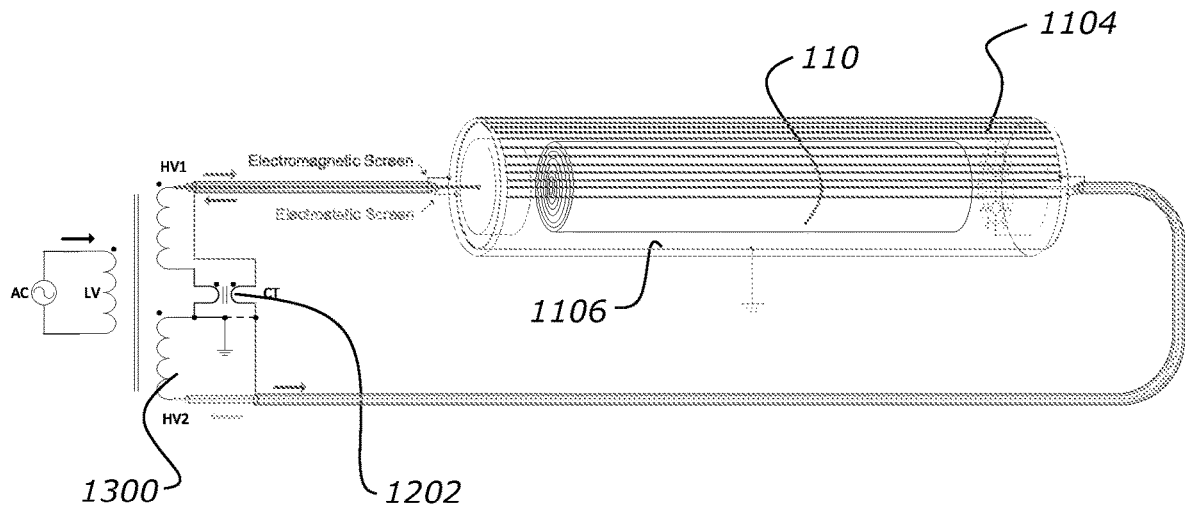
FIG. 13 shows an embodiment of the wood heating system of FIG. 1 in which a centre-ground bipolar HV supply is connected to the log.

FIG. 13 shows an embodiment of the wood heating system 100 in which a centre-ground bipolar HV supply 1300 is connected to the log 110. The current transformer 1202 supplies an exact replica of the log current, to cancel the external magnetic field, and allows the EM screen 1104 to be at any desired potential, including ground, while the ES screen prevents any displacement currents flowing through the CT windings 1202.

Figure 14:
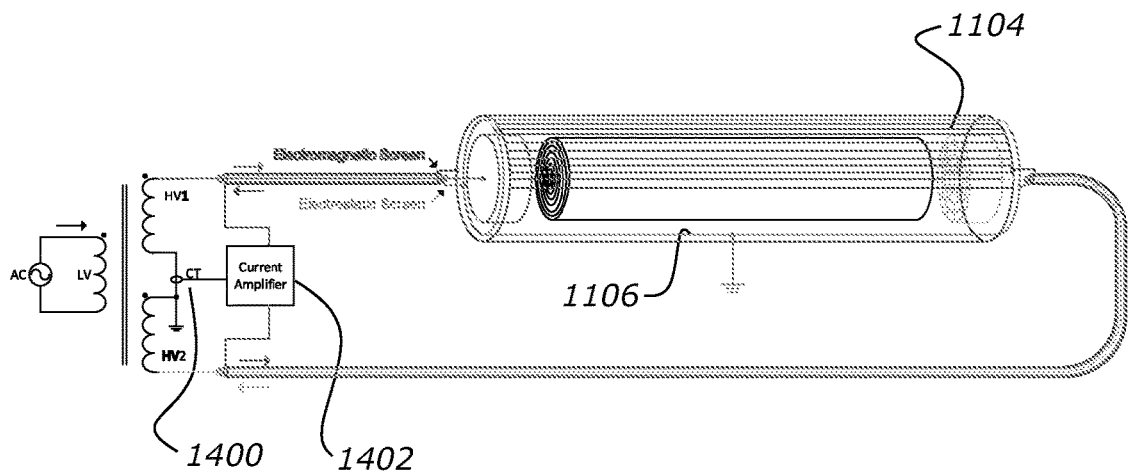
FIG. 14 shows an embodiment of the wood heating system of FIG. 1 in which a current transformer implements an active system rather than a passive system.

FIG. 14 shows an embodiment of the wood heating system 100 in which a current transformer 1400 implements an active system rather than a passive system by providing a signal corresponding to the log current to a current amplifier 1402. The amplifier 1402 drives a compensating current through the EM screen 1104 to eliminate external magnetic field. The electromagnetic screen 1104 may be grounded, or held at any other desired potential.

The embodiment shown in FIG. 14 has the potential to remove the need for the current transformer 1400 to be capable of driving the impedance of the EM screen 1104.

Figure 15:
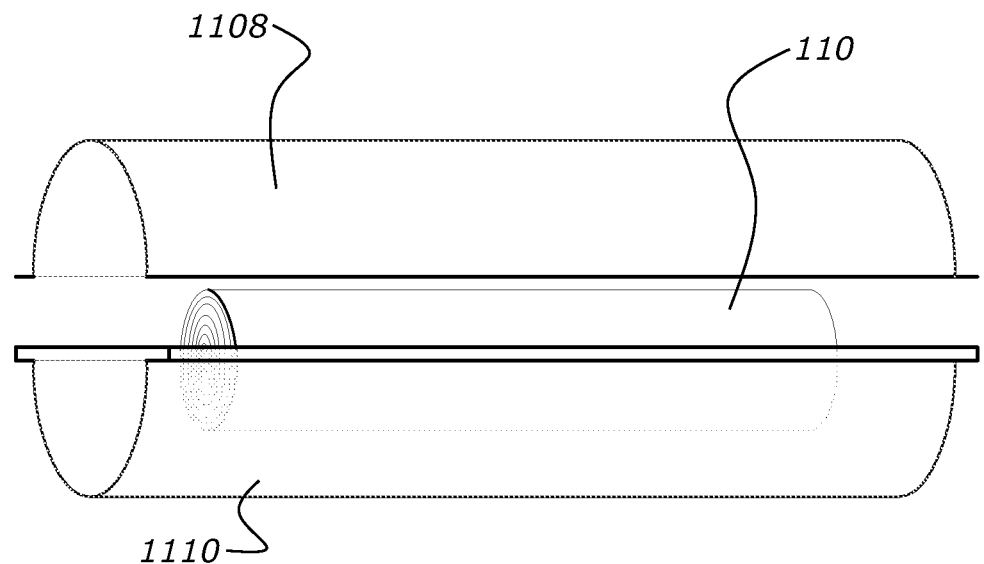
FIGS. 15 and 16 show an embodiment of the electrostatic and/or electromagnetic shielding/screening system for the wood heating system of FIG. 1 involving two half-pipes which may be combined to form an electromagnetic chamber.
Figure 16:
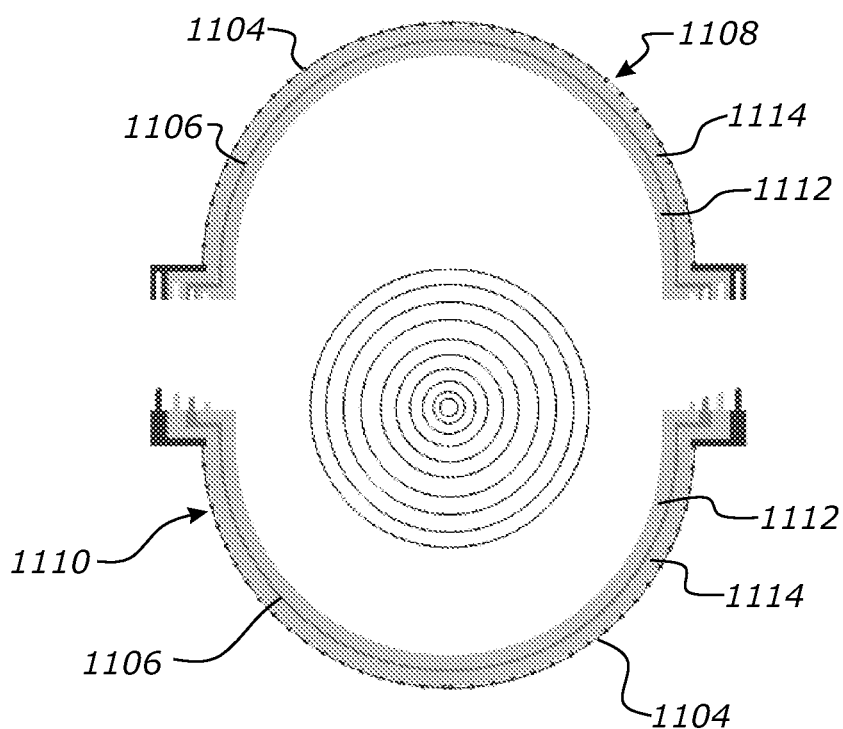

FIG. 15 and FIG. 16 show an embodiment of the wood heating system 100 in which the EM screen 1104 and ES screen 1106 are combined and incorporated in the form of two half-pipes 1108, 1110. The embodiment shown has a top half-pipe 1108 and a bottom half-pipe 1110, however, other arrangements are envisaged, such as two side half-pipes. Each half-pipe 1108, 1110 includes an inner insulating layer 1112 followed by a conductive ES screen 1106. In an embodiment the ES screen 1106 is formed from a thin sheet or foil of copper, aluminium, or other electrically conductive material.

A second insulating layer 1114 isolates the ES screen 1106 from the outer EM screen 1104. Means for electrically connecting the two halves of the screen, and maintaining satisfactory installation when the log is enclosed, are shown as a preferred embodiment.

When joined, the two half-pipes 1108, 1110 form an electromagnetic chamber.

Figure 17:
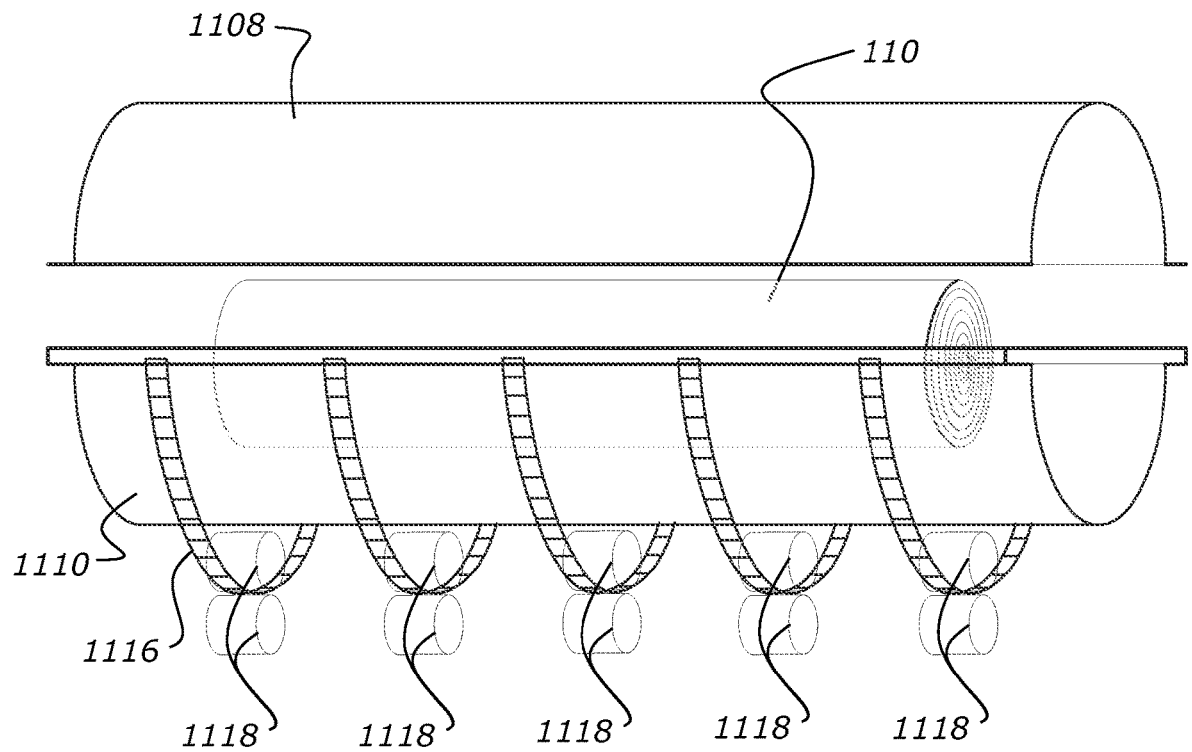
FIGS. 17 and 18 show an embodiment of the wood heating system of FIG. 1 in which a log is centred within an electromagnetic chamber during operation.
Figure 18:
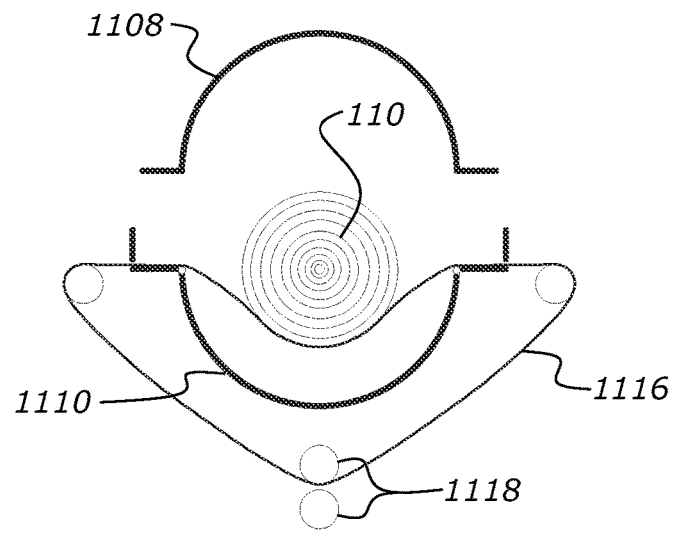

FIG. 17 and FIG. 18 show an embodiment of the wood heating system 100 in which a log 110 is centred within an electromagnetic chamber during operation.

Figure 19:
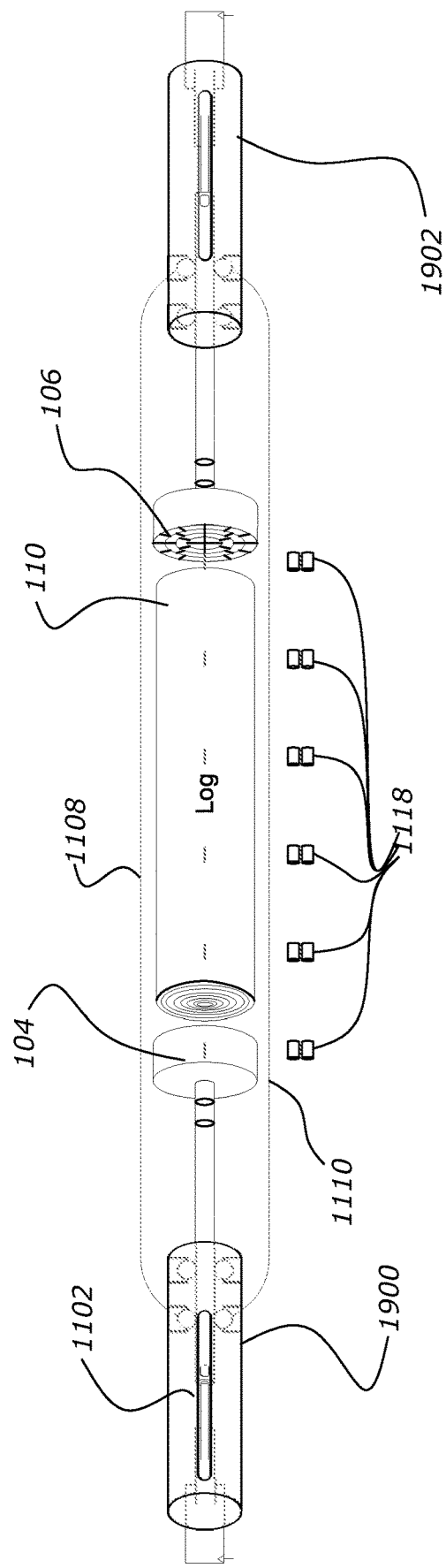
FIG. 19 shows an embodiment of the wood heating system of FIG. 1 that includes a screening system and means for positioning the electrodes with a controlled contact pressure.

FIG. 19 shows an embodiment of the wood heating system 100 that includes a screening system. Also shown is means for positioning the electrodes with a controlled contact pressure. With the top half-pipe 1108 lifted out of the way, a log 110 enters the system from a conveyor before the top half-pipe 1108 is again lowered into place. The position of the log 110 is adjusted by log centering actuators 1118.

First electrode assembly 104 and second electrode assembly 106 slide within a tube formed from the two half-pipes. In an embodiment spacing between the electrode assemblies is adjusted by a pair of pneumatic or hydraulic rams, which may be fitted with position sensors, indicated at 1900 and 1902. The force exerted by the rams 1900, 1902 can be controlled to provide controlled contact pressure to the log ends. Cardan joints 1120 are provided between the rams 1900, 1902 and the electrode assemblies 104, 106.

The rams may act to either push or pull the electrode assemblies onto the log ends. If the rams pull the electrode assemblies onto the log ends, using connecting rods, they can be placed above or below the axis of the log, reducing the overall maximum length or width occupied. The rams may be fitted with position sensors. This allows the log's length to be automatically determined by the energy determining algorithm/control system.

In an alternative embodiment (not illustrated), the top half-pipe is fixed in place above a conveyor and the log is raised into a centred position on insulating supports driven by pneumatic or hydraulic rams. The bottom half-pipe is then raised into place before electrical excitation is applied.

In an embodiment, the pneumatic or hydraulic rams which raise the log are fitted with load cells, such that the mass of the log is measured at the start and/or at the end of an excitation. This allows the mass reading to be sent to the energy determining algorithm/control system. Measuring before and after allows loss of moisture to be measured, as well as initial mass.

The foregoing description of the invention includes preferred forms thereof. Modifications may be made thereto without departing from the scope of the invention.

The invention claimed is:

1. Apparatus for determining different wood regions of a wood length, the apparatus comprising:
a first electrode assembly configured to connect to a first end of an elongate wood length and a second electrode assembly configured to connect to a second end of the wood length which is opposite to the first end, at least one of the first and second electrode assemblies comprising a plurality of electrode segments;
an electric power source configured to apply excitation to the first and second electrode assemblies, wherein each of the electrode segments includes an individual electrical connection to the electric power source;
a controller configured to monitor the current or voltage in each segment to determine an electrode segment current or voltage distribution and
to derive from the electrode segment current or voltage distribution at least one control volume, the or each control volume representing a volume of a wood region of the wood length.

2. The apparatus as claimed in claim 1, wherein the controller is configured to determine conductivity of the or each control volume.

3. The apparatus as claimed in claim 1, wherein the controller is configured to determine at least one dimension of the wood length or mass or volume of the wood length or moisture content or density of at least one of the or each control volume.

4. The apparatus as claimed in claim 1, wherein the controller is configured to determine at least one power parameter and a temperature change in the at least one control volume.

5. The apparatus as claimed in claim 4, wherein the at least one power parameter includes one or more of a resistance of the at least one control volume, a voltage across the at least one control volume, a current through the at least one control volume, a power dissipation density in the at least one control volume.

6. The apparatus as claimed in claim 3, wherein the wood region comprises at least one of a heartwood region, a sapwood region, or intermediate or transition wood regions of the wood length and the at least one dimension of the wood length includes at least one of a length of the wood length, a large end diameter, a small end diameter, a heartwood diameter at the large end, and a heartwood diameter at the small end of the wood length.

7. The apparatus as claimed in claim 1, wherein the at least one control volume comprises one or more nodes along a calculated dimension of the first end or the second end.

8. The apparatus as claimed in claim 1, wherein the controller is configured to determine energy to be applied to the wood length for treating the wood length.

9. The apparatus as claimed in claim 8, wherein the controller determines the energy to be applied from a plurality of process parameters including one or more of electrical power, total energy, energy of an excitation period, number of excitation periods, relaxation interval, number of control volumes in a heartwood region of the wood length, number of control volumes in a sapwood region of the wood length, multiplication coefficient for electrical conductivity.

10. The apparatus as claimed in claim 1, wherein one or more of the plurality of electrode segments further comprises a switch configured to disconnect current flow through that segment.

11. The apparatus as claimed in claim 10, wherein the one or more of the plurality of electrode segments may be configured to produce an electronic signal proportional to a current through that segment if the switch is not fitted or is fitted and is closed, or voltage across the switch if the switch is fitted and is open.

12. The apparatus as claimed in claim 1, wherein the controller is configured to selectively connect/disconnect electric power flow between the voltage source and the at least one electrode segment of the first and second electrode assemblies.

13. The apparatus as claimed in claim 1, wherein the wood region comprises one or more of heartwood or sapwood or intermediate or transition wood regions of the wood length.

14. The apparatus as claimed in claim 1, wherein each of the plurality of electrode segments comprise generally arcuate segments extending at least part of the way around a substantially flat face, the flat face configured to contact the ends of the wood length.

15. The apparatus as claimed in claim 1, wherein at least one of the first and second electrode assemblies comprises tessellating, or otherwise juxtaposed, electrode segments of any shape and size on a face, the face configured to contact the first or second end of the wood length.

16. The apparatus as claimed in claim 14, further comprising at least one pad inserted between the face of either or both of the first and second electrode assemblies and the respective ends of the wood length.

17. The apparatus as claimed in claim 16, wherein the at least one pad comprise a conformable material configured to be electrically conductive in itself, or non-conductive but filled with electrically conductive material.

18. The apparatus as claimed in claim 16, wherein the at least one pad is configured to be equally conductive in all directions or predominantly in the axial direction, and wherein the conductivity preferably being significantly equivalent to the most conductive region of the wood length in the axial direction.

19. A method for determining different wood regions of an elongate wood length comprising:
connecting a first electrode assembly to a first end of the wood length and connecting a second electrode assembly to a second end of the wood length opposite to the first end, at least one of the first or second electrode assemblies comprising a plurality of electrode segments;
energizing the plurality of electrode segments of each electrode assembly to determine a current or voltage distribution from an electrical sensor in the plurality of electrode segments; and
deriving from the electrode segment current or voltage distribution at least one control volume, the or each control volume representing a volume of a wood region of the wood length.

20. The method as claimed in claim 19, further comprising determining the conductivity of the control volume.

21. The method as claimed in claim 19, further comprising determining a target temperature to estimate energy required to treat the wood length.

22. The method as claimed in claim 19, further comprising determining one or more wood length parameters including one or more dimensions of the wood length or mass or volume of the wood length or moisture content or density of the at least one control volume.

23. The method as claimed in claim 19, further comprising determining at least one power parameter including one or more of a resistance of the at least one control volume, a voltage across the at least one control volume, a current through the at least one control volume, a power dissipation density in the at least one control volume.

24. The method as claimed in claim 19, further comprising selectively energizing or de-energizing the at least one electrode segment of the first and second electrode assemblies.

25. An apparatus for treating an elongate wood length comprising:
a controller configured to energize a first and a second electrode assembly, at least one of the first and second electrode assemblies comprising a plurality of electrode segments configured for connection to a first end of the wood length and a second end of the wood length opposite to the first end;
a measurement system comprising electrical sensors associated with each of the plurality of electrode segments, the measurement system configured to determine a current or voltage distributions across the first and/or second end of the wood length;
a circuit configured to receive and transmit data from the measurement system to the controller; the controller being configured to determine from the data a plurality of process parameters including temperature and/or estimated energy required to heat the wood length to a target temperature; and
a treatment system configured to treat the wood length to the target temperature.

26. The apparatus as claimed in claim 25, wherein the plurality of process parameters include one or more of temperature, electrical power, total energy, energy of an excitation period, number of excitation periods, relaxation interval, number of control volumes in a heartwood region of the wood length, number of control volumes in a sapwood region of the wood length, multiplication coefficient for electrical conductivity.

27. The apparatus as claimed in claim 25, wherein the treatment system comprises a wood heating apparatus configured to heat the wood length to the target temperature.

28. The apparatus as claimed in claim 25, wherein the data include data representing the present value of the current or voltage distributions.

* * * * *